United States Patent
Serradeil-Le Gal et al.

(10) Patent No.: US 6,596,732 B2
(45) Date of Patent: Jul. 22, 2003

(54) 1,3-DIHYDRO-2H-INDOL-2-ONE, PREPARATION METHOD AND PHARMACEUTICAL COMPOSITIONS CONTAINING SAME

(75) Inventors: Claudine Serradeil-Le Gal, Escalquens (FR); Bernard Tonnerre, Vailhauques (FR); Jean Wagnon, Montpellier (FR)

(73) Assignee: Sanofi-Synthelabo, Paris (FR)

( * ) Notice: Subject to any disclaimer, the term of this patent is extended or adjusted under 35 U.S.C. 154(b) by 0 days.

(21) Appl. No.: 10/203,730

(22) PCT Filed: Feb. 22, 2001

(86) PCT No.: PCT/FR01/00509

§ 371 (c)(1),
(2), (4) Date: Aug. 12, 2002

(87) PCT Pub. No.: WO01/64668

PCT Pub. Date: Sep. 7, 2001

(65) Prior Publication Data

US 2003/0109545 A1 Jun. 12, 2003

(30) Foreign Application Priority Data

Feb. 25, 2000 (FR) .............................................. 00 02488

(51) Int. Cl.[7] ........................ C07D 401/04; A61K 31/47
(52) U.S. Cl. ........................ 514/307; 514/418; 546/146; 546/147; 548/455
(58) Field of Search ................................ 546/146, 147; 548/455; 514/307, 418

(56) References Cited

U.S. PATENT DOCUMENTS 5,338,755 A    8/1994  Wagnon et al. ............. 514/423
5,594,023 A    1/1997  Wagnon et al. ............. 514/423

FOREIGN PATENT DOCUMENTS

| EP | 0 526 348 A | 2/1993 |
| WO | WO 95 18105 A | 7/1995 |

*Primary Examiner*—Zinna Northington Davis
(74) *Attorney, Agent, or Firm*—Paul E. Dupont; Michael D. Alexander

(57) ABSTRACT

The invention relates to compounds of formula:

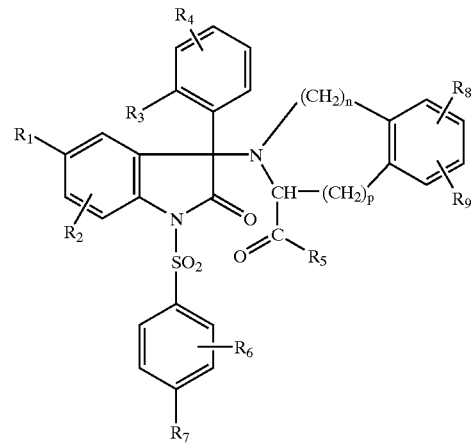

and their solvates and/or hydrates exhibiting an affinity and a selectivity for arginine-vasopressin $V_{1b}$ receptors or for both $V_{1b}$ and $V_{1a}$ receptors.

20 Claims, No Drawings

1,3-DIHYDRO-2H-INDOL-2-ONE, PREPARATION METHOD AND PHARMACEUTICAL COMPOSITIONS CONTAINING SAME

This application is a 371 of PCT/FR01/00509 filed Feb. 22, 2001.

A subject-matter of the present invention is novel 1,3-dihydro-2H-indol-2-one derivatives, a process for their preparation and the pharmaceutical compositions comprising them.

The compounds according to the present invention exhibit an affinity and a selectivity for arginine-vasopressin (AVP) $V_{1b}$ receptors or for both $V_{1b}$ and $V_{1a}$ receptors.

AVP is a hormone known for its antidiuretic effect and its effect in regulating arterial pressure. It stimulates several types of receptors: $V_1$ ($V_{1a}$, $V_{1b}$) or $V_2$. These receptors are located in particular in the liver, vessels (coronary, renal, cerebral), platelets, kidney, uterus, adrenal glands, pancreas, central nervous system or pituitary gland. AVP thus exerts cardiovascular, hepatic, pancreatic, antidiuretic and platelet-aggregating effects and effects on the central and peripheral nervous system and on the uterine sphere.

The localization of various receptors is described in: S. Jard et al., Vasopressin and oxytocin receptors: an overview, in Progress in Endocrinology, H. Imura and K. Shizurne ed., Experta Medica, Amsterdam, 1988, 1183–1188, and in the following articles: J. Lab. Clin. Med., 1989, 114 (6), 617–632 and Pharmacol. Rev., 1991, 43 (1), 73–108.

More particularly, AVP $V_{1a}$ receptors are located in numerous peripheral organs and in the brain. they have been cloned in the rat and man and they regulate the majority of known effects of AVP: platelet aggregation; uterine contractions; vessel contraction; the secretion of aldosterone, of cortisol, of CRF (corticotropin-releasing factor) and of adrenocorticotrophic hormone (ACTH); heptatic glycogenolysis, cell proliferation and the main central effects of AVP (hypothermia, memory, and the like).

The $V_{1b}$ receptors were initially identified in the adenohypophysis of various animal species (rat, pig, cow, sheep, and the like), including in man (S. Jard et al., Mol. Pharmacol., 1986, 30, 171–177; Y. Arsenijevic et al., J. Endocrinol., 1994, 141, 383–391; J. Schwartz et al., Endocrinology, 1991, 129 (2), 1107–1109; Y. de Keyser et al., FEBS Letters, 1994, 356, 215–220), where they stimulate the release of adrenocorticotrophic hormone by AVP and potentiate the effects of CRF on the release of ACTH (G. E. Gillies et al., Nature, 1982, 299, 355). In the hypothalamus, the $V_{1b}$ receptors also induce a direct release of CRF (Neuroendocrinology, 1994, 60, 503–508) and are, in these various respects, implicated in stress situations.

These $V_{1b}$ receptors have been cloned in the rat, man and mouse (Y. de Keyser, FEBS Letters, 1994, 356, 215–220; T. Sugimoto et al., J. Biol. Chem., 1994, 269 (43), 27088–27092; M. Saito et al., Biochem. Biophys. Res. Commun., 1995, 212 (3), 751–757; S.J. Lolait et al., Neurobiology, 1996, 92, 6783–6787; M. A. Ventura et al., Journal of Molecular Endocrinology, 1999, 22, 251–260) and various studies (in situ hybridization, PCR (Polymerase Chain Reaction), and the like) reveal ubiquitous localization of these receptors in various central tissues (brain, hypothalamus and adenohypophysis, in particular) and peripheral tissues (kidney, pancreas, adrenal glands, heart, lungs, intestine, stomach, liver, mesentery, bladder, thymus, spleen, uterus, retina, thyroid, and the like) and in some tumours (hypophyseal or pulmonary tumours, and the like), suggesting a broad biological and/or pathological role of these receptors and potential involvement in various diseases.

By way of examples, in the rat, studies have shown that AVP, via the $V_{1b}$ receptors, regulates the endocrine pancreas, stimulating the secretion of insulin and of glucagon (B. Lee et al., Am. J. Physiol., 269 (Endocrinol. Metab. 32), E1095-E1100, 1995) or the production of catecholamines in the medulloadrenal, which is the site of a local synthesis of AVP (E. Grazzini et al., Endocrinology, 1996, 137 (a), 3906–3914). Thus, in the last tissue, AVP, via these receptors, would have a crucial role in some types of suprarenal pheochromocytomas which secrete AVP and which, for this reason, bring about a sustained production of catecholamines which are the cause of hypertensions which are resistant to angiotensin-II receptor antagonists and to converting enzyme inhibitors. The adrenal cortex is also rich in $V_{1a}$ receptors involved in the production of gluco- and mineralocorticoids (aldosterone and cortisol). Via these receptors, AVP (circulating or synthesized locally) can bring about production of aldosterone with an effectiveness comparable to that of angiotensin II (G. Guillon et al., Endocrinology, 1995, 136 (3), 1285–1295). Cortisol is a powerful regulator of the production of ACTH, the stress hormone.

Recent studies have also shown that the adrenal glands are capable of directly releasing CRF and/or ACTH via the activation of the $V_{1b}$ and/or $V_{1a}$ receptors carried by the cells of the medulla (G. Mazzocchi et al., Peptides, 1997, 18(2), 191–195; E. Grazzini et al., J. Clin. Endocrinol. Metab., 1999, 84 (6), 2195–2203).

The $V_{1b}$ receptors are also regarded as a label for ACTH-secreting tumours, which are some pituitary tumours and some bronchial (small cell lung cancers or SCLC), pancreatic, adrenal and thyroid carcinomas, resulting in some cases in Cushing's syndrome (J. Berthcrat et al., Eur. J. Endocrinol., 1996, 135, 173; G. A. Wittert et al., Lancet, 1990, 335, 991–994; G. Dickstein et al., J. Clin. Endocrinol. Metab., 1996, 81 (8), 2934–2941). The $V_{1a}$ receptors are, for their part, a more specific label for small cell lung cancers (SCLC) (P. J. Woll et al., Biochem. Biophys. Res. Commun., 1989, 164 (1), 66–73). Thus, the compounds according to the present invention are obvious diagnostic tools and offer a novel therapeutic approach in the proliferation and detection of these tumours, at an early stage too (radiolabelling; SPECT (Single Photon Emission Computed Tomography); PET Scan (Positron Emission Tomography Scanner)).

The lavish presence of the messenger of the $V_{1b}$ receptors in the stomach and intestine suggests involvement of AVP via this receptor in the release of gastrointestinal hormones, such as cholecystokinin, gastrin or secretin (T. Sugimoto et al., Molecular cloning and functional expression of $V_{1b}$ receptor gene, in Neurohypophysis: Recent Progress of Vasopressin and Oxytocin Research; T. Saito, K. Kurokawa and S. Yoshida ed., Elvesier Science, 1995, 409–413).

1,3-Dihydro-2H-indol-2-one derivatives have been disclosed in some patent applications as ligands of the arginine-vasopressin and/or oxytocin receptors: mention may be made of Patent Applications WO 93/15051, EP 636 608, EP 636 609, WO 95/18105, WO 97/15556 and WO 98/25901.

To date, no nonpeptide compound having an affinity and a selectivity for arginine-vasopressin $V_{1b}$ receptors or for both $V_{1b}$ and $V_{1a}$ receptors is known.

Novel 1,3-dihydro-2H-indol-2-one derivatives have now been found which exhibit an affinity and a selectivity for arginine-vasopressin $V_{1b}$ receptors or for both $V_{1b}$ and $V_{1a}$ receptors.

These compounds can be used for the preparation of medicaments of use in the treatment or prevention of any pathology where arginine-vasopressin and/or the $V_{1b}$ receptors or both the $V_{1b}$ receptors and the $V_{1a}$ receptors are implicated, in particular in the treatment or prevention of conditions of the cardiovascular system, for example hypertension, of the central nervous system, for example stress, anxiety, depression, obsessive-compulsive disorder or panic attacks, of the renal system or of the gastric system and in the treatment of small cell lung cancers, of obesity, of type-II diabetes, of insulin resistance, of hypertriglyceridaemia, of atherosclerosis, of Cushing's syndrome or of any pathology resulting from stress and chronic stress conditions.

Thus, according to one of its aspects, the subject-matter of the present invention is compounds of formula:

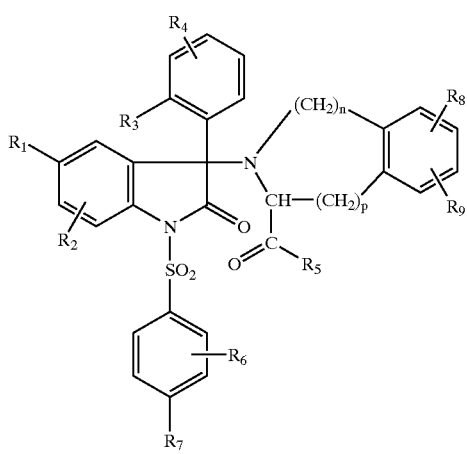

(I)

in which:

n is 0, 1 or 2 and p is 0, 1 or 2; the sum n+p being equal to 1 or 2;

$R_1$ represents a halogen atom; a $(C_1-C_4)$ alkyl; a $(C_1-C_4)$ alkoxy; a trifluoromethyl radical; or a trifluoromethoxy-radical;

$R_2$ represents a hydrogen atom; a halogen atom; a $(C_1-C_4)$alkyl; a $(C_1-C_4)$alkoxy; or a trifluoromethyl radical;

or else $R_2$ is in the 6-position of the indol-2-one ring and $R_1$ and $R_2$ together-represent the bivalent trimethylene radical;

$R_3$ represents a halogen atom; a hydroxyl; a $(C_1-C_2)$alkyl; a $(C_1-C_2)$alkoxy; or a trifluoromethoxy radical;

$R_4$ represents a hydrogen atom; a halogen atom; a $(C_1-C_2)$alkyl; or a $(C_1-C_2)$alkoxy;

or else $R_4$ is in the 3-position of the phenyl and $R_3$ and $R_4$ together represent the methylenedioxy radical;

$R_5$ represents an ethylamino group; a dimethylamino group; an azetidin-1-yl radical; or a $(C_1-C_2)$ alkoxy;

$R_6$ represents a $(C_1-C_4)$alkoxy;

$R_7$ represents a $(C_1-C_4)$alkoxy;

$R_8$ represents a hydrogen atom; a halogen atom; a $(C_1-C_4)$alkyl; or a $(C_1-C_4)$alkoxy;

$R_9$ represents a hydrogen atom; a halogen atom; a $(C_1-C_4)$alkyl; or a $(C_1-C_4)$alkoxy;

and their solvates and/or hydrates.

The compounds of formula (I) comprise at least 2 asymmetric carbon atoms. The optically pure isomers of the compounds of formula (I) and their mixtures in any proportion form part of the invention.

The term "halogen atom" is understood to mean a chlorine, bromine, fluorine or iodine atom.

The term "alkyl" or the term "alkoxy" are respectively understood to mean a linear or branched alkyl or alkoxy radical respectively.

In the compounds of formula (I), the radical:

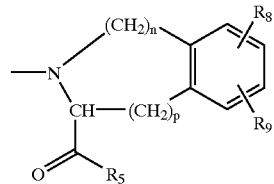

represents one of the following radicals:

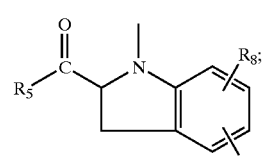

(A)

(B)

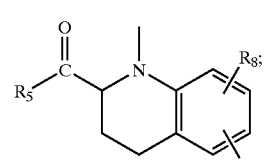

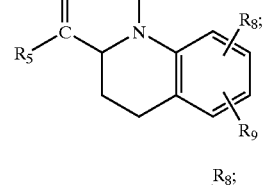

(C)

(D)

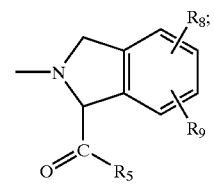

(E)

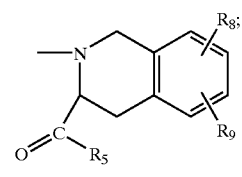

According to the present invention, preference is given to the compounds of formula (I) in which:

n is 0, 1 or 2 and p is 0, 1 or 2; the sum n+p being equal to 1 or 2;

$R_1$ represents a halogen atom; a $(C_1-C_4)$ alkyl; a trifluoromethyl radical; or a trifluoromethoxy radical;

$R_2$ represents a hydrogen atom; a halogen atom; a $(C_1-C_4)$alkyl; a $(C_1-C_4)$alkoxy; or a trifluoromethyl radical;

or else $R_2$ is in the 6-position of the indol-2-one ring and $R_1$ and $R_2$ together represent the bivalent trimethylene radical;

$R_3$ represents a halogen atom; a hydroxyl; or a ($C_1$–$C_2$) alkoxy;

$R_4$ represents a hydrogen atom; a halogen atom; a ($C_1$–$C_2$)alkyl; or a ($C_1$–$C_2$)alkoxy;

or else $R_4$ is in the 3-position of the phenyl and $R_3$ and $R_4$ together represent the methylenedioxy radical;

$R_5$ represents an ethylamino group; a dimethylamino group; an azetidin-1-yl radical; or a ($C_1$–$C_2$) alkoxy;

$R_6$ represents a ($C_1$–$C_4$)alkoxy;

$R_7$ represents a ($C_1$–$C_4$)alkoxy;

$R_8$ represents a hydrogen atom;

$R_8$ represents a hydrogen atom;

and their solvates and/or hydrates.

According to the present invention, the compounds of formula (I) having an (A), (D) or (E) radical are preferred.

According to the present invention, preference is given to the compounds of formula (I) in which $R_1$ represents a chlorine atom, a methyl radical or a trifluoromethoxy radical.

According to the present invention, preference is given to the compounds of formula (I) in which $R_2$ represents a hydrogen atom or is in the 4- or 6-position of the indol-2-one and represents a chlorine atom, a methyl radical, a methoxy radical or a trifluoromethyl radical.

According to the present invention, preference is given to the compounds of formula (I) in which $R_3$ represents a chlorine atom or a methoxy radical.

According to the present invention, preference is given to the compounds of formula (I) in which $R_4$ represents a hydrogen atom or is in the 3- or 4-position of the phenyl and represents a methoxy radical; or else $R_4$ is in the 3-position of the phenyl and together with $R_3$ represent a methylenedioxy radical.

According to the present invention, preference is given to the compounds of formula (I) in which $R_5$ represents a dimethylamino group, an azetidin-1-yl radical or a methoxy radical.

According to the present invention, preference is given to the compounds of formula (I) in which $R_6$ is in the 2-position of the phenyl and represents a methoxy radical.

According to the present invention, preference is given to the compounds of formula (I) in which $R_7$ represents a methoxy radical.

According to the present invention, preference is given to the compounds of formula (I) in which $R_8$ and $R_8$ each represent a hydrogen atom.

Preference is more particularly given to the compounds of formula (I) in which:

the

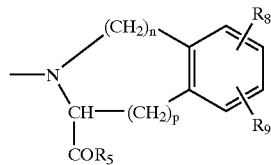

radical represents an (A), (D) or (E) radical;

$R_1$ represents a chlorine atom or a methyl radical;

$R_2$ represents a hydrogen atom or is in the 4- or 6-position of the indol-2-one and represents a chlorine atom, a methyl radical or a methoxy radical;

$R_3$ represents a methoxy radical or a chlorine atom;

$R_4$ represents a hydrogen atom or is in the 3- or 4-position of the phenyl and represents a methoxy radical;

or else $R_4$ is in the 3-position of the phenyl and together with $R_3$ represent a methylenedioxy radical;

$R_8$ represents a dimethylamino group or a methoxy radical;

$R_6$ is in the 2-position of the phenyl and represents a methoxy radical;

$R_8$ represents a methoxy radical;

$R_8$ and $R_8$ represent a hydrogen atom;

and their solvates and/or hydrates.

According to the present invention, preference is given to the compounds of formula (I) in the form of optically pure isomers.

More particularly, preference is given to the optically pure isomers of the compounds of formula:

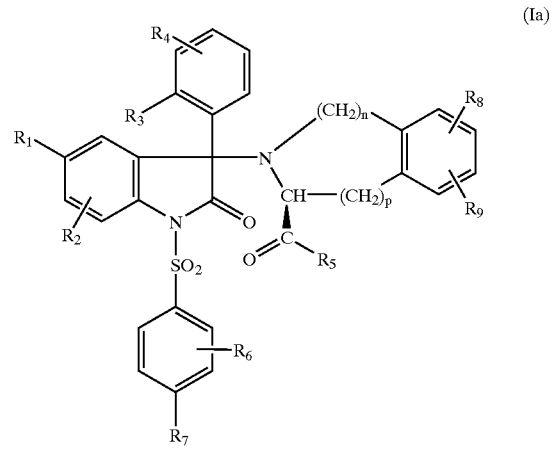

(Ia)

in which n, p, $R_1$, $R_2$, $R_3$, $R_4$, $R_5$, $R_6$, $R_7$, $R_8$ and $R_8$ are as defined for a compound of formula (I), the carbon atom carrying the $COR_5$ substituent has the (S) configuration and the carbon atom in the 3-position of the indol-2-one has either the (R) configuration or the (S) configuration.

Preference is very particularly given to the levorotatory isomer of the compounds of formula (Ia).

The following compounds:

(3S)-2-[5-Chloro-1-[(2,4-dimethoxyphenyl)sulphonyl]-3-(2-methoxyphenyl)-2-oxo-2,3-dihydro-1H-indol-3-yl]-N,N-dimethyl-1,2,3,4-tetrahydroisoquinoline-3-carboxamide, levorotatory isomer;

(1S)-2-[5-Chloro-1-[(2,4-dimethoxyphenyl)sulphonyl]-3-(2-methoxyphenyl)-2-oxo-2,3-dihydro-1H-indol-3-yl]-N,N-dimethyl-1,2,3,4-tetrahydroisoquinoline-1-carboxamide, levorotatory isomer;

(2S)-1-[5-Chloro-1-[(2,4-dimethoxyphenyl)sulphonyl]-3-(2-methoxyphenyl)-2-oxo-2,3-dihydro-1H-indol-3-yl]-N,N-dimethyl-2,3-dihydro-1H-indole-2-carboxamide, levorotatory isomer;

Methyl ester of (3S)-2-[5-chloro-1-[(2,4-dimethoxyphenyl)sulphonyl]-3-(2-methoxyphenyl)-2-oxo-2,3-dihydro-1H-indol-3-yl]-1,2,3,4-tetrahydroisoquinoline-3-carboxylic acid, levorotatory isomer;

(3S)-2-[5,6-Dichloro-1-[(2,4-dimethoxyphenyl) sulphonyl]-3-(2-methoxyphenyl)-2-oxo-2,3-dihydro-1H-indol-3-yl]-N,N-dimethyl-1,2,3,4-tetrahydroisoquinoline-3-carboxamide, levorotatory isomer;

(3S)-2-[5-Chloro-1-[(2,4-dimethoxyphenyl)sulphonyl]-3-(2-methoxyphenyl)-6-methyl-2-oxo-2,3-dihydro- 1H-indol-3-yl]-N,N-dimethyl-1,2,3,4-tetrahydroisoquinoline-3-carboxamide, levorotatory isomer;

(3S)-2-[5-Chloro-1-[(2,4-dimethoxyphenyl)sulphonyl]-3-(2-methoxyphenyl)-2-oxo-2,3-dihydro-1H-indol-3-yl]-6,7-dimethoxy-N,N-dimethyl-1,2,3,4-tetrahydroisoquinoline-3-carboxamide, levorotatory isomer;

(3S)-2-[5-Chloro-3-(2-chlorophenyl)-1-[(2,4-dimethoxyphenyl)sulphonyl]-2-oxo-2,3-dihydro-1H-indol-3-yl]-N,N-dimethyl-1,2,3,4-tetrahydroisoquinoline-3-carboxamide, levorotatory isomer;

(3S)-2-[5-Chloro-1-[(2,4-dimethoxyphenyl)sulphonyl]-3-(2,3-dimethoxyphenyl)-2-oxo-2,3-dihydro-1H-indol-3-yl]-N,N-dimethyl-1,2,3,4-tetrahydroisoquinoline-3-carboxamide, levorotatory isomer;

(3S)-2-[5-Chloro-1-[(2,4-dimethoxyphenyl)sulphonyl]-3-(2,4-dimethoxyphenyl)-2-oxo-2,3-dihydro-1H-indol-3-yl]-N,N-dimethyl-1,2,3,4-tetrahydroisoquinoline-3-carboxamide, levorotatory isomer;

(3S)-2-[5-Chloro-3-(1,3-benzodioxol-4-yl)-1-[(2,4-dimethoxyphenyl)sulphonyl]-2-oxo-2,3-dihydro-1H-indol-3-yl]-N,N-dimethyl-1,2,3,4-tetrahydroisoquinoline-3-carboxamide, levorotatory isomer;

(3S)-2-[5,6-Dichloro-3-(2-chlorophenyl)-1-[(2,4-dimethoxyphenyl)sulphonyl]-2-oxo-2,3-dihydro-1H-indol-3-yl]-N,N-dimethyl-1,2,3,4-tetrahydroisoquinoline-3-carboxamide, levorotatory isomer;

(3S)-2-[5-Chloro-3-(2-chlorophenyl)-1-[(2,4-dimethoxyphenyl)sulphonyl]-6-methoxy-2-oxo-2,3-dihydro-1H-indol-3-yl]-N,N-dimethyl-1,2,3,4-tetrahydroisoquinoline-3-carboxamide, levorotatory isomer;

(3S)-2-[4-Chloro-1-[(2,4-dimethoxyphenyl)sulphonyl]-3-(2-methoxyphenyl)-5-methyl-2-oxo-2,3-dihydro-1H-indol-3-yl]-N,N-dimethyl-1,2,3,4-tetrahydroisoquinoline-3-carboxamide, levorotatory isomer;

and their solvates and/or hydrates are more particularly preferred.

According to another of its aspects, a subject-matter of the present invention is a process for the preparation of the compounds of formula (I), their solvates and/or their hydrates, characterized in that:

a compound of formula:

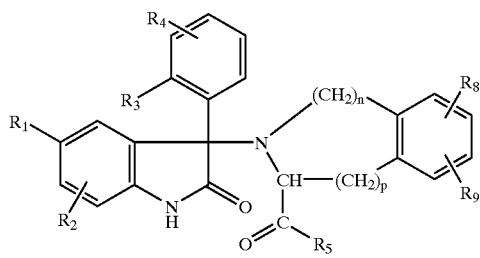

(II)

in which n, p, $R_1$, $R_2$, $R_3$, $R_4$, $R_5$, $R_8$ and $R_9$ are as defined for a compound of formula (I), is reacted, in the presence of a base, with a halide of formula:

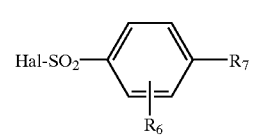

(III)

in which $R_6$ and $R_7$ are as defined for a compound of formula (I) and Hal represents a halogen atom.

The reaction is carried out in the presence of a strong base, such as a metal hydride, for example sodium hydride, or an alkali metal alkoxide, for example potassium tert-butoxide, in an anhydrous solvent, such as N,N-dimethylformamide or tetrahydrofuran, and at a temperature of between −70° C. and +60° C. The reaction is preferably carried out by using a compound of formula (III) in which Hal=Cl.

The compounds of formula (I) thus obtained can subsequently be separated from the reaction mixture and purified according to conventional methods, for example by crystallization or chromatography.

The compounds of formula (II) are prepared by the reaction of a 3-halo-1,3-dihydro-2H-indol-2-one compound of formula:

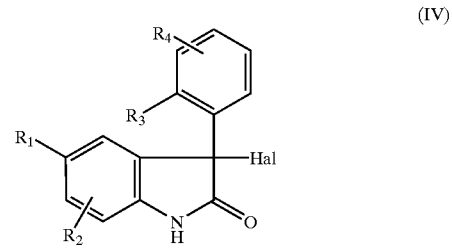

(IV)

in which $R_1$, $R_2$, $R_3$ and $R_4$ are as defined for a compound of formula (I) and Hal represents a halogen atom, preferably chlorine or bromine, with a compound of formula:

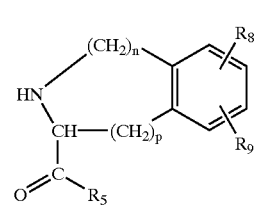

(V)

in which n, p and $R_5$, $R_8$ and $R_9$ are as defined for a compound of formula (I). The reaction is carried out in the presence of a base, such as diisopropylethylamine or triethylamine, in an inert solvent, such as dichloromethane, chloroform or tetrahydrofuran or a mixture of these solvents, and at a temperature of between ambient temperature and the reflux temperature of the solvent.

The compounds of formula (III) are known or prepared by known methods, such as those disclosed in EP-0 469 984 B and WO 95/18105. For example, the compounds of formula (III) can be prepared by halogenation of the corresponding benzenesulphonic acids or of their salts, for example of their sodium or potassium salts. The reaction is carried out in the presence of a halogenating agent, such as phosphorus oxychloride, thionyl chloride, phosphorus trichloride, phosphorus tribromide or phosphorus pentachloride, without a solvent or in an inert solvent, such as a halogenated hydrocarbon or N,N-dimethylformamide, and at a temperature of between −10° C. and 200° C.

2,4-Dimethoxybenzenesulphonyl chloride is prepared according to J. Am. Chem. Soc., 1952, 74, 2008. 3,4-Dimethoxybenzenesulphonyl chloride is commercially available or prepared according to J. Med. Chem., 1977, 20 (10), 1235–1239.

The compounds of formula (IV) are known and are prepared according to known methods, such as those disclosed in WO 95/18105.

For example, a compound of formula:

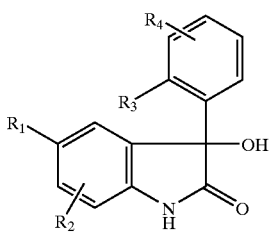

(VI)

in which $R_1$, $R_2$, $R_3$ and $R_4$ are as defined for a compound of formula (I), is converted into a compound of formula (IV) in which Hal=Cl by the action of thionyl chloride in the presence of a base, such as pyridine, in an inert solvent, such as dichloromethane, and at a temperature between 0° C. and ambient temperature.

According to another example of the preparation of the compounds of formula (IV), a compound of formula:

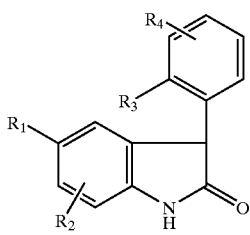

(VII)

in which $R_1$, $R_2$, $R_3$ and $R_4$ are as defined for a compound of formula (I), is converted into a compound of formula (IV) by means of a halogenating agent, such as bromine, according to the process described in Farm. Zh. (Kiev), 1976, 5, 30–33.

The compounds of formula (VI) are known and are prepared according to known methods, such as those disclosed in WO 95/18105.

For example, a compound of formula (VI) is prepared by reaction of a 1H-indole-2,3-dione derivative of formula:

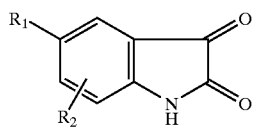

(VIII)

in which $R_1$ and $R_2$ are as defined for a compound of formula (I), with an organomagnesium derivative of formula:

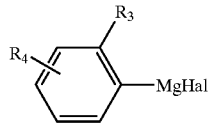

(IX)

in which $R_3$ and $R_4$ are as defined for a compound of formula (I) and Hal represents a halogen atom, preferably bromine or iodine, in an inert solvent, such as tetrahydrofuran or diethyl ether, and at a temperature of between 0° C. and the reflux temperature of the solvent.

A compound of formula (VI) in which $R_3$ is as defined for a compound of formula (I) and $R_4$, which is other than hydrogen, is in the 3- or 6-position of the phenyl can also be prepared by the reaction of a compound of formula:

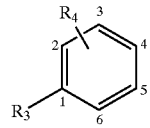

(XVI)

in which $R_3$ is as defined for a compound of formula (I) and $R_4$ is in the 2- or 5-position of the phenyl, with a lithium derivative, such as n-butyllithium, and then the lithiated intermediate thus obtained is reacted with a compound of formula (VIII). The reaction is carried out in a solvent, such as diethyl ether, tetrahydrofuran, hexane or a mixture of these solvents, at a temperature of between −70° C. and ambient temperature.

The 1H-indole-2,3-dione derivatives (VIII) are commercially available or prepared according to the methods described in Tetrahedron Letters, 199,8, 39, 7679–7682; Tetrahedron Letters, 1994, 35, 7303–7306; J. Org. Chem., 1977, 42 (8), 1344–1348; J. Org. Chem., 1952, 17, 149–156; J. Am. Chem. Soc., 1946, 68, 2697–2703, Organic Syntheses, 1925, V, 71–74 and Advances in Heterocyclic Chemistry, A. R. Katritzky and A. J. Boulton, Academic Press, New York, 1975, 18, 2–58.

The organomagnesium derivatives (IX) are prepared according to conventional methods well known to a person skilled in the art.

A compound of formula (VI) can also be prepared by air oxidation of a compound of formula (VII) in the presence of a base, such as sodium hydride, and in the presence of dimethyl disulphide.

Specifically, the compounds of formula (VI) in which $R_3$=($C_1$–$C_2$)alkoxy and $R_4$=H or else $R_3$=$R_4$=($C_1$–$C_2$) alkoxy with $R_4$ in the 3- or 6-position of the phenyl, $R_2$ is other than a halogen atom and $R_1$ is as defined for a compound of formula (I) can be prepared by following the process described in SCHEME 1.

SCHEME 1

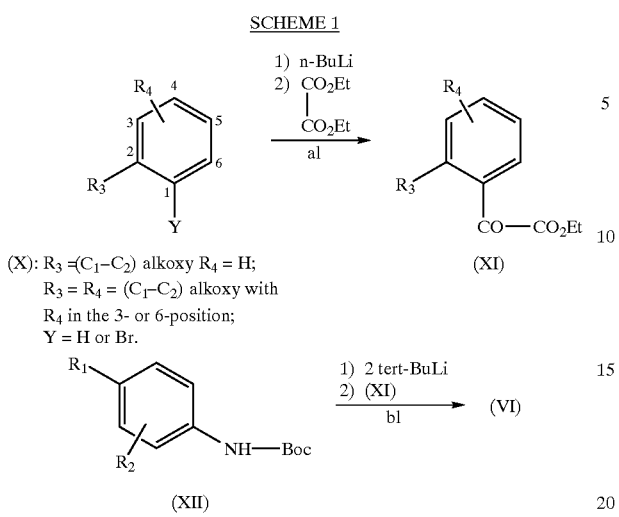

(X): $R_3 = (C_1-C_2)$ alkoxy $R_4 = H$;
$R_3 = R_4 = (C_1-C_2)$ alkoxy with
$R_4$ in the 3- or 6-position;
$Y = H$ or $Br$.

In stage a1 of SCHEME 1, a compound of formula (X) is first of all reacted with a lithium derivative, such as n-butyllithium, in the absence or in the presence of a base, such as N,N,N',N'-tetramethylenediamine, and then the lithiated intermediate thus obtained is reacted with diethyl oxalate to give the compound of formula (XI). The reaction is carried out in an inert solvent, such as diethyl ether or tetrahydrofuran, and at a temperature of between −70° C. and ambient temperature.

In stage b1, a compound of formula (XII) is first of all reacted with two equivalents of a lithium derivative, such as tert-butyllithium, and then the lithiated intermediate obtained is reacted with the compound of formula (XI) to give the expected compound of formula (VI). The reaction is carried out in an inert solvent, such as diethyl ether or tetrahydrofuran, and at a temperature of between −70° C. and ambient temperature.

The compounds of formula (X) are commercially available or are synthesized in a conventional way.

The compounds of formula (XII) are prepared by reaction of the corresponding aniline derivatives with di-tert-butyl dicarbonate according to conventional methods.

The compounds of formula (VII) are known and are prepared according to known methods, such as those disclosed in WO 95/18105 or in J. Org. Chem., 1968, 33, 1640–1643.

The compounds of formula (V) are known or are prepared according to known methods. Thus, for example, the compounds of formula (V) in which $R_5$ represents an ethylamino or dimethylamino group or an azetidin-1-yl radical are prepared according to SCHEME 2 below, in which Pr represents an N-protecting group, in particular tert-butoxycarbonyl or 9-fluorenylmethoxycarbonyl, and n, p, $R_8$ and $R_9$ are as defined for a compound of formula (I).

SCHEME 2

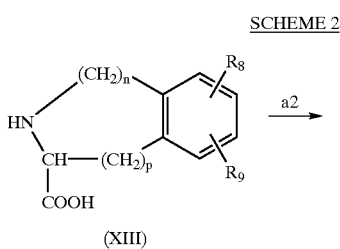

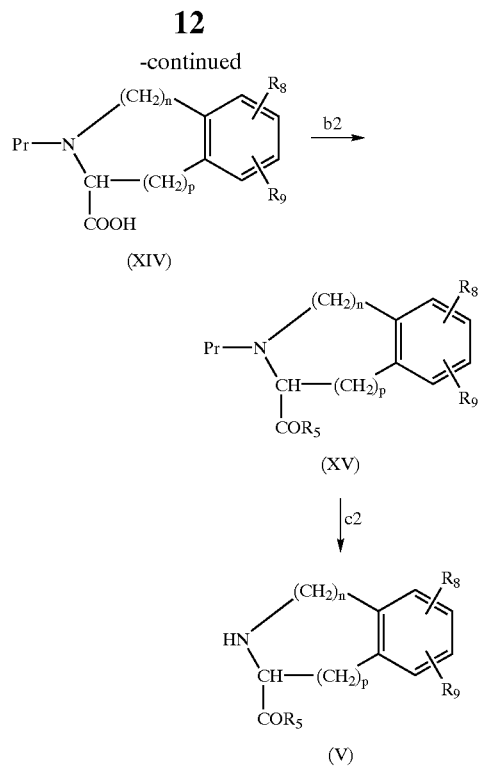

In stage a2 of SCHEME 2, the nitrogen atom of the compound of formula (XIII) is protected according to conventional methods to obtain a compound of formula (XIV). Some of the compounds of formula (XIV) are commercially available.

The acid (XIV) is reacted in stage b2 with ethylamine, dimethylamine or azetidine according to conventional peptide coupling methods to give the compound of formula (XV), which is deprotected in stage c2 according to known methods to give the expected compound of formula (V). In particular, when Pr represents a 9-fluorenylmethoxycarbonyl group, deprotection is carried out using the method described in Synthetic Communications, 1994, 24 (2), 187–195.

The compounds of formula (V) in which $R_5$ represents a $(C_1-C_2)$alkoxy are known or are prepared according to known methods, such as, for example, by an esterification reaction starting with the acids of formula (XIII), or according to the methods described in Tetrahedron Letters, 1986, 27, 2409–2410; J. Am. Chem. Soc., 1970, 92, 2476–2488; Tetrahedron Asymmetry, 1998, 9, 4295–4299; J. Med. Chem., 1994, 37, 3956–3968; J. Chem. Soc. Perkin Trans 1, 1977, 596–600; Gazz. Chim. Ital., 1976, 106, 65; Chem. Pharm. Bull., 1983, 31, 312–314; J. Med. Chem., 1983, 26, 1267–1277; J. Org. Chem., 1997, 62, 7679–7689; J. Med. Chem., 1992, 35, 1942–1953; Justus Liebigs Ann. Chem., 1976, 367–382; J. Org. Chem., 1978, 43, 2115–2119; Tetrahedron Letters, 1997, 38, 6977–6980; Helv. Chim. Acta, 1959, 42, 2431–2436.

The acids of formula (XIII) are commercially available or are prepared according to known methods. Thus, for example:
  2,3-Dihydro-1H-indole-2-carboxylic acids are prepared according to J. Med. Chem., 1983, 26, 394–403; Agric. Biol. Chem., 1987, 51, 1833–1838; J. Med. Chem., 1983, 26, 1267–1277; Helv. Chim. Acta, 1962, 45, 638; Helv. Chim. Acta, 1968, 51, 1476.
  1,2,3,4-Tetrahydroquinoline-2-carboxylic acids are prepared according to J. Org. Chem., 1990, 55, 738–741; J. Med. Chem., 1992, 35, 1942–1953;

Isoindoline-1-carboxylic acids are prepared according to J. Heterocyclic. Chem., 1984, 21, 1355–1360;

1,2,3,4-Tetrahydroisoquinoline-3-carboxylic acids are prepared according to Synthesis, 1992, 11, 1157–1160; Int. J. Peptide Protein Res., 1994, 43, 62–68; Liebigs Ann./Recueil, 1997, 3, 533–540; J. Med. Chem., 1988, 31, 2092–2097; J. Chem. Soc., 1938, 172–175; J. Chem. Soc., 1950, 1534–1537; Synthesis, 1990, 550–556; Heterocycles, 1992, 34, 757–764; J. Med. Chem., 1983, 26, 1267–1277;

1,2,3,4-Tetrahydroisoquinoline-1-carboxylic acids are prepared according to J. Med. Chem., 1993, 36, 314–319 or according to WO 93/12091.

When it is desired to prepare an optically pure compound of formula (I), an optically pure compound of formula (II) is preferably reacted with a compound of formula (III) according to the process of the invention.

The optically pure compounds of formula (II) are prepared by reaction of the racemic compound of formula. (IV) with an optically pure compound of formula (V), followed by separation of the mixture of diastereoisomers according to conventional methods, for example by crystallization or chromatography.

Alternatively, the mixture of diastereoisomers of the compound of formula (II) can be reacted with the compound of formula (III) and the mixture of diastereoisomers of the compound of formula (I) thus obtained can be separated.

During any one of the stages for the preparation of the compounds of formula (I) or of the intermediate compounds of formula (II), (IV), (V) or (VI), it may be necessary and/or desirable to protect the reactive or sensitive functional groups, such as amine, hydroxyl or carboxyl groups, present on any one of the molecules concerned. This protection can be achieved by using conventional protecting groups, such as those described in Protective Groups in Organic Chemistry, J. F. W. McOmie, published by Plenum Press, 1973, in Protective Groups in Organic Synthesis, T. W. Greene and P. G. M. Wutts, published by John Wiley and Sons, 1991 or in Protecting Groups, Kocienski P. J., 1994, Georg Thieme Verlag. The protecting groups can be removed at an appropriate subsequent stage using methods known to a person skilled in the art which do not affect the remainder of the molecule concerned.

The N-protecting groups optionally used are conventional N-protecting groups well known to a person skilled in the art, such as, for example, the tert-butoxycarbonyl, fluorenylmethoxycarbonyl, benzyl, benzhydrylidene or benzyloxycarbonyl group.

The compounds of formula (II) are novel and form part of the invention.

Thus, according to another of its aspects, a subject-matter of the invention is compounds of formula:

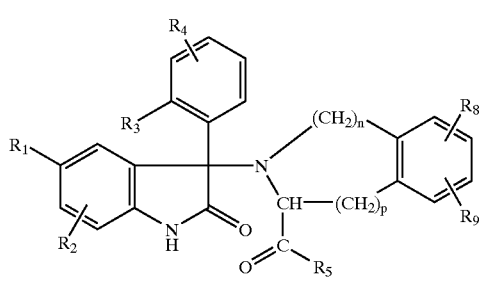

(II)

in which:

n is 0, 1 or 2 and p is 0, 1 or 2; the sum n+p being equal to 1 or 2;

$R_1$ represents a halogen atom; a ($C_1$–$C_4$) alkyl; a ($C_1$–$C_4$) alkoxy; a trifluoromethyl radical; or a trifluoromethoxy radical;

$R_2$ represents a hydrogen atom; a halogen atom; a ($C_1$–$C_4$)alkyl; a ($C_1$–$C_4$)alkoxy; or a trifluoromethyl radical;

or else $R_2$ is in the 6-position of the indol-2-one ring and $R_1$ and $R_2$ together represent the bivalent trimethylene radical;

$R_3$ represents a halogen atom; a hydroxyl; a ($C_1$–$C_2$)alkyl; a ($C_1$–$C_2$)alkoxy; or a trifluoromethoxy radical;

$R_4$ represents a hydrogen atom; a halogen atom; a ($C_1$–$C_2$) alkyl; or a ($C_1$–$C_2$) alkoxy;

or else $R_4$ is in the 3-position of the phenyl and $R_3$ and $R_4$ together represent the methylenedioxy radical;

$R_5$ represents an ethylamino group; a dimethylamino group; an azetidin-1-yl radical; or a ($C_1$–$C_2$) alkoxy;

$R_8$ represents a hydrogen atom; a halogen atom; a ($C_1$–$C_4$) alkyl; or a ($C_1$–$C_4$) alkoxy;

$R_8$ represents a a hydrogen atom; a halogen atom; a ($C_1$–$C_4$) alkyl; or a ($C_1$–$C_4$) alkoxy;

and their salts with inorganic or organic acids, in the form of optically pure isomers or in the form of a mixture of diastereoisomers or in the form of a racemic mixture.

The salts of the compounds of formula.(II) comprise those with inorganic or organic acids which make possible suitable separation or crystallization of the compounds of formula (II), such as the hydrochloride, hydrobromide, oxalate, maleate, succinate, fumarate, citrate or acetate.

The compounds of above formula (I) also comprise those in which one or more hydrogen or carbon atoms have been replaced by their radioactive isotope, for example tritium or carbon-14. Such labelled compounds are of use in research, metabolism or pharmacokinetic studies or in biochemical assays as receptor ligand.

The compounds according to the invention have formed the subject of biochemical studies.

The affinity of the compounds of formula (I) according to the invention for arginine-vasopressin $V_{1b}$ receptors was determined in vitro by using the method described by Y. De Keyser et al., FEBS Letters, 1994, 356, 215–220. This method consists in studying in vitro the displacement of tritiated arginine-vasopressin ([$^3$H]-AVP) at the $V_{1b}$ receptors present on adenohypophysal membrane or cell preparations carrying rat or human $V_{1b}$ receptors. The 50% inhibitory concentrations ($IC_{50}$) for the attachment of tritiated arginine-vasopressin of the compounds according to the invention are low and vary from $10^{-6}$ to $10^{-9}$M, more particularly from $10^{-7}$ to $10^{-9}$M.

The affinity of the compounds of formula (I) according to the invention for arginine-vasopressin $V_{1a}$ receptors was determined in vitro using the method described by M. Thibonnier et al., J. Biol. Chem., 1994, 269, 3304–3310. This method consists in studying in vitro the displacement of tritiated arginine-vasopressin ([$^3$H]-AVP) at the $V_{1a}$ receptors present on membrane or cell preparations carrying rat or human $V_{1a}$ receptors. Some of the compound of formula (I) also exhibit an affinity for arginine-vasopressin $V_{1a}$ receptors, with $IC_{50}$ values which vary from $10^{-6}$ to $10^{-9}$M, more particularly from $10^{-7}$ to $10^{-8}$M.

The affinity of the compounds of formula (I) according to the invention for vasopressin $V_2$ receptors has also been studied (method described by M. Birnbaumer et al., Nature (Lond.), 1992, 357, 333–335). The compounds studied have little or no affinity for the $V_2$ receptors.

The compounds of the present invention are in particular active principles of pharmaceutical compositions, the toxicity of which is compatible with their use as medicaments.

According to another of its aspects, the present invention relates to the use of the compounds of formula (I), of their solvates and/or of their hydrates which are pharmaceutically acceptable for the preparation of medicaments intended for the treatment of any pathology where arginine-vasopressin and/or its $V_{1b}$ receptors or both its $V_{1b}$ receptors and its $V_{1a}$ receptors are implicated.

According to another of its aspects, the present invention relates to the use of the compounds of formula (I), of their solvates and/or of their hydrates which are pharmaceutically acceptable in the preparation of medicaments intended for the treatment of pathologies of the cardiovascular system, of the central nervous system, of the renal system or of the gastric system and of small cell lung cancers, obesity, type-II diabetes, insulin resistance, hypertriglyceridaemia, atherosclerosis, Cushing's syndrome or any pathology resulting from stress and chronic stress conditions.

Thus, the compounds according to the invention may be used, in man or in animals, in the treatment or prevention of various vasopressin-dependent conditions, such as cardiovascular conditions, for example hypertension, pulmonary hypertension, cardiac insufficiency, myocardial infarction or coronary vasospasm, in particular in smokers, Raynaud's syndrome, unstable angina and PTCA (percutaneous transluminal coronary angioplasty), cardiac ischaemia or haemostasis disturbances; conditions of the central nervous system, such as migraine, cerebral vasospasm, cerebral haemorrhage, cerebral oedema, depression, anxiety, stress, obsessive-compulsive disorder, panic attacks, psychotic states or memory disorders, for example; conditions of the renal system, such as renal vasospasm, necrosis of the renal cortex or nephrogenic diabetes insipidus; conditions of the gastric system, such as gastric vasospasm, cirrhosis of the liver, ulcers or the pathology of vomiting, for example nausea, including nausea due to chemotherapy or travel sickness; or diabetic nephropathy. The compounds according to the invention can also be used in the treatment of disorders of sexual behaviour; in women, the compounds according to the invention can be used to treat dysmenorrhoea or premature labour. The compounds according to the invention can also be used in the treatment of small cell lung cancers; hyponatremic encephalopathy; pulmonary syndrome; Ménière's disease; glaucoma; cataracts; obesity; type-II diabetes; atherosclerosis; Cushing's syndrome; insulin resistance; or hypertriglyceridaemia; or in post-operative treatments, in particular after abdominal surgery.

The compounds according to the invention can also be used in the treatment or prevention of any pathology resulting from stress, such as fatigue and its syndromes, ACTH-dependent disorders, cardiac disorders, pain, modifications in gastric emptying, in faecal excretion (colitis, irritable bowel syndrome or Crohn's disease) or in acid secretion, hyperglycaemia, immunosuppression, inflammatory processes (rheumatoid arthritis and osteoarthritis), multiple infections, cancers, asthma, psoriasis, allergies and various neuropsychiatric disorders, such as anorexia nervosa, bulimia, mood disorders, depression, anxiety, sleep disorders, panic states, phobias, obsession, disorders of pain perception (fibromyalgia), neurodegenerative diseases (Alzheimer's disease, Parkinson's disease or Huntington's disease), substance dependence, haemorrhagic stress, muscle spasms or hypoglycaemia. The compounds according to the invention can also be used in the treatment or prevention of chronic stress conditions, such as immunodepression, fertility disorders or dysfunctionings of the hypothalamopituitaryadrenal axis.

The compounds according to the invention can also be used as psychostimulants, resulting in an increase in alertness or emotional reactivity to the surroundings and making adaptation easier.

The compounds of above formula (I), their solvates and/or their hydrates which are pharmaceutically acceptable can be used at daily doses of 0.01 to 100 mg per kilo of body weight of the mammal to be treated, preferably at daily doses of 0.1 to 50 mg/kg. In man, the dose can preferably vary from 0.1 to 4000 mg per day, more particularly from 0.5 to 1000 mg, depending upon the age of the subject to be treated or the type of treatment; prophylactic or curative.

For their use as medicaments, the compounds of formula (I) are generally administered in dosage units. The said dosage units are preferably formulated in pharmaceutical compositions in which the active principle is mixed with one or more pharmaceutical excipients.

Thus, according to another of its aspects, the present invention relates to pharmaceutical compositions including, as active principle, a compound of formula (I), one of its solvates and/or one of its hydrates which are pharmaceutically acceptable.

In the pharmaceutical compositions of the present invention for administration by the oral, sublingual, inhaled, subcutaneous, intramuscular, intravenous, transdermal, local or rectal route, the active principles can be administered in single-dose administration forms, as a mixture with conventional pharmaceutical vehicles, to animals and human beings. The appropriate single-dose administration forms comprise forms by the oral route, such as tablets, gelatin capsules, powders, granules and oral solutions or suspensions, sublingual and buccal administration forms, aerosols, topical administration forms, implants, subcutaneous, intramuscular, intravenous, intranasal or intraocular administration forms and rectal administration forms.

When a solid composition is prepared in the form of tablets or gelatin capsules, a mixture of pharmaceutical excipients is added to the micronized or nonmicronized active principle, which mixture can be composed of diluents, such as, for example, lactose, microcrystalline cellulose, starch or dicalcium phosphate, of binders, such as, for example, polyvinylpyrrolidone or hydroxypropylmethylcellulose, of disintegrating agent, such as crosslinked polyvinylpyrrolidone or crosslinked carboxymethylcellulose, of flow agents, such as silica or talc, or of lubricants, such as magnesium stearate, stearic acid, glyceryl tribehenate or sodium stearylfumarate.

Wetting agents or surfactants, such as sodium lauryl sulphate, polysorbate 80 or poloxamer 188, can be added to the formulation.

The tablets can be prepared by various techniques: direct tableting, dry granulation, wet granulation or hot-melt.

The tablets can be bare or sugar-coated (with sucrose, for example) or coated with various polymers or other appropriate materials.

The tablets can have a flash, delayed or sustained release by preparing polymeric matrices or by using specific polymers when forming the thin film.

The gelatin capsules may be soft or hard and may or may not be coated with a thin film, so as to have a flash, sustained or delayed activity (for example via an enteric form).

They can comprise not only a solid formulation formulated as above for tablets but also liquids or semi-solids.

A preparation in the form of a syrup or elixir can comprise the active principle in conjunction with a sweetener, preferably a calorie-free sweetener, methylparaben and propylparaben, as antiseptic, a flavouring agent and an appropriate colorant.

The water-dispersible powders or granules can comprise the active principle as a mixture with dispersing agents, wetting agents or suspending agents, such as polyvinylpyrrolidone, as well as with sweeteners or flavour enhancers.

For rectal administration, recourse is had to suppositories which are prepared with binders which melt at the rectal temperature, for example cocoa butter or polyethylene glycols.

For parenteral, intranasal or intraocular administration, use is made of aqueous suspensions, isotonic saline solutions or sterile and injectable solutions which comprise pharmacologically compatible dispersing agents and/or solubilizing agents, for example propylene glycol.

Thus, to prepare an aqueous solution which can be injected by the intravenous route, use may be made of a cosolvent, such as, for example, an alcohol, such as ethanol, or a glycol, such as polyethylene glycol or propylene glycol, and of a hydrophilic surfactant, such as polysorbate 80 or poloxamer 188. To prepare an oily solution which can be injected by the intramuscular route, the active principle can be dissolved with a triglyceride or a glyceryl ester.

For local administration, use may be made of creams, ointments, gels, eyewashes or sprays.

For transdermal administration, use may be made of patches in multilaminar or reservoir form, in which the active principle can be in alcoholic solution, or sprays.

For administration by inhalation, use is made of an aerosol comprising, for example, sorbitan trioleate or oleic acid and trichlorofluoromethane, dichlorofluoromethane, dichlorotetrafluoroethane, freon substitutes or any other biologically compatible propellant gas; use may also be made of a system comprising the active principle, alone or in combination with an excipient, in powder form.

The active principle can also be presented in the form of a complex with a cyclodextrin, for example α, β- or γ-cyclodextrin or 2-hydroxypropyl-β-cyclodextrin.

The active principle can also be formulated in the form of microcapsules or microspheres, optionally with one or more vehicles or additives.

Use may be made of implants among the sustained-release forms of use in the case of chronic treatments. These implants can be prepared in the form of an oily suspension or in the form of a suspension of microspheres in an isotonic medium.

The active principle of formula (I) is present in each dosage unit in the amounts suited to the daily doses envisaged. In general, each dosage unit is suitably adjusted according to the dosage and the type of administration provided, for example tablets, gelatin capsules and the like, sachets, blisters, syrups and the like, or drops, so that such a dosage unit comprises from 0.1 to 1000 mg of active principle, preferably from 0.5 to 250 mg, which has to be administered one to four times daily.

Although these dosages are examples of average situations, there may be specific cases where higher or lower dosages are appropriate; such dosages also form part of the invention. According to the usual practice, the dosage appropriate to each patient is determined by the physician according to the method of administration and the age, the weight and the response of the said patient.

The compositions of the present invention can comprise, in addition to the compounds of formula (I), their solvates and/or their hydrates which are pharmaceutically acceptable, other active principles which can be of use in the treatment of the disorders or diseases indicated above.

Thus, another subject-matter of the present invention is pharmaceutical compositions comprising several active principles in combination, one of which is a compound according to the invention.

Thus, according to the present invention, pharmaceutical compositions can be prepared which comprise a compound according to the invention in combination with a compound which has an effect on the CRF receptors.

The compounds according to the invention can also be used for the preparation of compounds for veterinary use.

The following PREPARATIONS and EXAMPLES illustrate the invention without, however, limiting it.

Use is made, in the Preparations and in the Examples, of the following abbreviations:

ether: diethyl ether
iso ether: diisopropyl ether
DMF: N,N-dimethylformamide
THF: tetrahydrofuran
DCM: dichloromethane
AcOEt: ethyl acetate
DIPEA: diisopropylethylamine
TFA: trifluoroacetic acid
Boc: tert-butoxycarbonyl
Cbz: benzyloxycarbonyl
BOP: benzotriazol-1-yloxytris(dimethyl-amino) phosphonium hexafluorophosphate
PyBOP: benzotriazol-1-yloxytripyrrolidino-phosphonium hexafluorophosphate
DCC: 1,3-dicyclohexylcarbodiimide
HOBT: 1-hydroxybenzotriazole hydrate
M.p.: melting point
AT: ambient temperature
B.p.: boiling point
HPLC: high performance liquid chromatography.

The proton magnetic resonance spectra ($^1$H NMR) are recorded at 200 MHz in $d_6$-DMSO using the $d_6$-DMSO peak as reference. The chemical shifts δ are expressed in parts per million (ppm). The signals observed are expressed thus: s: singlet; bs: broad singlet; d: doublet; dd: double doublet; t: triplet; q: quartet; up: unresolved peak; mt: multiplet.

PREPARATIONS

Preparations of the compounds of formula (IV).

Preparation 1.1

3,5-Dichloro-3-(2-methoxyphenyl)-1,3-dihydro-2H-indol-2-one (IV): $R_1$=Cl; $R_2$=H; $R_3$=OCH$_3$; $R_4$=H; Hal=Cl
A) 5–7Chloro-3-hydroxy-3-(2-methoxyphenyl)-1,3-dihydro-2H-indol-2-one.

This compound is prepared according to the procedure disclosed in WO 95/18105. A solution of 2-methoxyphenylmagnesium bromide is prepared from 16 g of magnesium in 35 ml of ether and from a solution of 124 g of 1-bromo-2-methoxybenzene in 175 ml of ether. This solution is added dropwise under an argon atmosphere to a mixture, cooled beforehand in an ice bath, of 30 g of 5-chloro-1H-indole-2,3-dione in 250 ml of THF and then the mixture is left stirring while allowing the temperature to rise to AT. After stirring for 1 hour at AT, the reaction mixture is slowly poured onto a saturated NH$_4$Cl solution and the THF is evaporated under vacuum. The precipitate formed is filtered off and is washed with iso ether. 42 g of the expected product are obtained, which product is used as is in the following stage.

B) 3,5-Dichloro-3-(2-methoxyphenyl)-1,3-dihydro-2H-indol-2-one.

This compound is prepared according to the procedure disclosed in WO 95/18105. A mixture of 12.71 g of the compound obtained in the preceding stage in 105 ml of DCM is cooled to 0° C., 5.3 ml of pyridine are added and then 4.9 ml of thionyl chloride are added. After stirring for 30 minutes, water is added to the reaction mixture and the DCM is evaporated under vacuum. The precipitate formed is filtered off, washed three times with water and then three times with iso ether, and dried. 13.66 g of the expected product are obtained, which product is used as is.

Preparation 1.2

3,5,6-Trichloro-3-(2-methoxyphenyl)-1,3-dihydro-2H-indol-2-one (IV): $R_1$=Cl; $R_2$=6-Cl; $R_3$=OCH$_3$; $R_4$=H; Hal=Cl A) 5,6-Dichloro-1H-indole-2,3-dione.

This compound is prepared according to the procedure described in J. Am. Chem. Soc., 1946, 68, 2697–2703 or according to the procedure described in J. Org. Chem., 1952, 17, 149–156.

B) 5,6-Dichloro-3-hydroxy-3-(2-methoxyphenyl)-1,3-dihydro-2H-indol-2-one.

5.57 g of 1-bromo-2-methoxybenzene are added dropwise to a suspension of 0.72 g of magnesium in 15 ml of ether comprising a few iodine crystals, the reflux being maintained when it has begun. At the end of the addition, the mixture is heated at reflux for 2 hours. A suspension of 2.7 g of 5,6-dichloro-1H-indole-2,3-dione in 30 ml of THF is subsequently added and the mixture is heated at reflux for 30 minutes. After cooling to AT, the reaction mixture is poured onto a water/ice/concentrated HCl mixture and extracted with AcOEt, the organic phase is dried over Na$_2$SO$_4$ and the solvent is evaporated under vacuum. The residue is triturated in iso ether under warm conditions and the precipitate formed is filtered off and washed with ether. 3 g of the expected product are obtained.

C) 3,5,6-Trichloro-3-(2-methoxyphenyl)-1,3-dihydro-2H-indol-2-one.

A suspension of 1.5 g of the compound obtained in the preceding stage in 30 ml of DCM is cooled in an ice bath, 0.56 ml of pyridine is added and then 0.5 ml of thionyl chloride is added. After stirring for 1 hour at AT, the reaction mixture is diluted by addition of DCM, the organic phase is washed with water until the pH is neutral and dried over Na$_2$SO$_4$, and the solvent is evaporated under vacuum. 1.5 g of the expected product are obtained in the form of foams, which product is used as is.

Preparation 1.3

3,5-Dichloro-3-(2-methoxyphenyl)-6-methyl-1,3-dihydro-2H-indol-2-one (IV): $R_1$=Cl; $R_2$=6-CH$_3$; $R_3$=OCH$_3$; $R_4$=H; Hal=Cl A) Ethyl 2-(2-Methoxyphenyl)-2-oxoacetate.

A solution of 27 g of 1-bromo-2-methoxybenzene in 270 ml of ether is cooled to −70° C. under an argon atmosphere, 90 ml of a 1.6M solution of n-butyllithium in pentane are added dropwise and then the mixture is left stirring for 45 minutes. 78 ml of diethyl oxalate are rapidly added and the mixture is left stirring while allowing the temperature to rise to AT. After stirring for 1 hour at AT, a saturated NH$_4$Cl solution is added to the reaction mixture, separation by settling is carried out, the aqueous phase is extracted with ether, the combined organic phases are washed with water and with a saturated NaCl solution and dried over Na$_2$SO$_4$, and the solvents are evaporated under vacuum. The excess diethyl oxalate is removed by vacuum distillation (B.p.= 870° C. under 2000 Pa). The resulting product is chromatographed on silica gel, elution being carried out with a DCM/hexane (50/50, v/v) mixture and then with DCM. The product obtained is purified by vacuum distillation. 13 g of the expected product are obtained, B.p.=110° C. under 3 Pa.

B) 5-Chloro-3-hydroxy-3-(2-methoxyphenyl)-6-methyl-1,3-dihydro-2H-indol-2-one.

a) tert-Butyl 4-chloro-3-methylphenyl-carbamate.

A mixture of 10 g of 4-chloro-3-methylaniline and 15.26 g of di-tert-butyl dicarbonate in 50 ml of dioxane is left stirring for 24 hours at AT. The reaction mixture is concentrated under vacuum and the residue is chromatographed on silica gel, elution being carried out with the gradient of the DCM/hexane mixture from (50/50, v/v) to (70/30, v/v). 5.6 g of the expected product are obtained, which product is used as is.

b) A solution of 5 g of tert-butyl 4-chloro-3-methylphenylcarbamate in 45 ml of ether is cooled to −70° C. under an argon atmosphere, 30 ml of a 1.5M solution of tert-butyllithium in pentane are added dropwise, and the mixture is left stirring for 1 hour while raising the temperature to −10° C. and left stirring at −10° C. for 1 hour 45 minutes. The reaction mixture is cooled to −70° C., a solution of 5 g of the compound obtained in stage A in 25 ml of THF is added dropwise, and the mixture is left stirring for 1 hour while allowing the temperature to rise to −300° C. and then overnight while allowing the temperature to rise to AT. A saturated NH$_4$Cl solution is added to the reaction mixture, the THF is evaporated, the resulting aqueous phase is extracted three times with AcOEt, the organic phase is washed with water and with a saturated NaCl solution and dried over Na$_2$SO$_4$, the solvent is partially evaporated and the crystalline product is filtered off. 2.6 g of the expected product are obtained, M.p.=254–256° C.

C) 3,5-Dichloro-3-(2-methoxyphenyl)-6-methyl-1,3-dihydro-2H-indol-2-one.

A mixture of 1.3 g of the compound obtained in stage B in 30 ml of DCM is cooled to 0° C., 0.5 ml of pyridine is added and then 0.763 g of thionyl chloride is added, and the mixture is left stirring for 2 hours after having allowed the temperature to rise to AT.

Water and DCM are added to the reaction mixture, after separating by settling the organic phase is washed four times with water and dried over Na$_2$SO$_4$, and the solvent is evaporated under vacuum. The expected product is obtained in the form of a foam, which product is used as is in Preparation 3.7.

Preparation 1.4

3-Bromo-5-chloro-3-(2-chlorphenyl)-1,3-dihydro-2H-indol-2-one (IV): $R_1$=Cl; $R_2$=H; $R_3$=Cl; $R_4$=H; Hal=Br This compound is prepared according to the procedures disclosed in WO 95/18105 in stages A), B) and C) of Preparation 2.

Preparation 1.5

3,5-Dichloro-3-(2,3-dimethoxyphenyl)-1,3-dihydro-2H-indol-2-one (IV): $R_1$=Cl; $R_2$=H; $R_3$=OCH$_3$; $R_4$=3-OCH$_3$; Hal=Cl A) Ethyl 2-(2,3-Dimethoxyphenyl)-2-oxoacetate.

A mixture of 27.6 g of 1,2-dimethoxybenzene in 160 ml of ether is cooled to −40° C, 250 ml of a 1.6M solution of n-butyllithium in hexane are added dropwise and then the mixture is left stirring for 24 hours while allowing the temperature to rise to AT. The reaction mixture is cooled to −20° C., 136 ml of diethyl oxalate are rapidly added and the mixture is left stirring while allowing the temperature to rise to AT. After stirring for 30 minutes at AT, the reaction mixture is poured onto a saturated NH$_4$Cl solution, separated by settling is-carried out, the aqueous phase is extracted with ether, the combined organic phases are washed twice with water and dried over Na$_2$SO$_4$, and the solvents are evaporated under vacuum. The excess diethyl oxalate is removed by vacuum distillation (B.p.=90° C. under 2400 Pa). The crude resulting product is chromatographed on silica gel, elution being carried out with a heptane/iso ether (90/10, v/v) mixture. 25 g of the expected product are obtained, which product is used as is in the following stage.

B) 5-Chloro-3-hydroxy-3-(2,3-dimethoxyphenyl)-1,3-dihydro-2H-indol-2-one.

a) tert-Butyl 4-chlorophenylcarbamate.

A mixture of 12.7 g of 4-chloroaniline and 22 g of di-tert-butyl dicarbonate in 60 ml of dioxane is left stirring for 24 hours at AT. The reaction mixture is concentrated under vacuum, the residue is taken up in pentane, and the precipitate formed is filtered off and dried. 2.2.5 g of the expected product are obtained.

b) A mixture of 11.4 g of tert-butyl 4-chlorophenylcarbamate in 100 ml of ether is cooled to −40° C. under a dry nitrogen atmosphere, 80 ml of a 1.5M solution of tert-butyllithium in pentane are added dropwise and the mixture is left stirring for 3 hours at −20° C. The reaction mixture is cooled to −40° C., a solution of 14 g of the compound obtained in stage A in 50 ml of THF is added over one hour and the mixture is left stirring for 4 days at AT. The reaction mixture is poured onto a saturated NH$_4$Cl solution and the precipitate formed is filtered off and dried. 10.2 g of the expected product are obtained, which product is used as is in the following stage.

C) 3,5-Dichloro-3-(2,3-dimethoxyphenyl)-1,3-dihydro-2H-indol-2-one.

1.27 ml of pyridine and then 1.2 ml of thionyl chloride are added, at 0° C., to a mixture of 3.35 g of the compound obtained in stage B in 30 ml of DCM and the mixture is left stirring for 2 hours. The reaction mixture is washed [lacuna] water and dried over Na$_2$SO$_4$ and the solvent is evaporated under vacuum. The expected product is obtained, which product is used as is in Preparation 3.9.

Preparation 1.6

3,5-Dichloro-3-(2,4-dimethoxyphenyl)-1,3-dihydro-2H-indol-2-one (IV): R$_1$=Cl; R$_2$=H; R$_3$=OCH$_3$; R$_4$=4-OCH$_3$; Hal=Cl A) 5-Chloro-3-hydroxy-3-(2,4-dimethoxyphenyl)-1,3-dihydro-2H-indol-2-one A solution of 2,4-dimethoxyphenylmagnesium bromide is prepared from 2.2 g of magnesium in 10 ml of TFH and from a solution of 18 g of 1-bromo-2,4-dimethoxybenzene in 40 ml of THF. This solution is added dropwise to a mixture of 5 g of 5-chloro-1H-indole-2,3-dione in 50 ml of THF at a temperature of 30° C. and then the mixture is heated at reflux for 2 hours. The reaction mixture is cooled to AT, is poured onto a saturated NH$_4$Cl solution and extracted with AcOEt, the organic phase is washed with water and dried over Na$_2$SO$_4$, and the solvent is evaporated under vacuum. 7.2 g of the expected product are obtained after crystallization from iso ether under warm conditions.

B) 3,5-Dichloro-3-(2,4-dimethoxyphenyl)-1,3-dihydro-2H-indol-2-one.

A mixture of 3.8 g of the compound obtained in the preceding stage and 1.35 ml of pyridine in 80 ml of DCM is cooled to 0° C., 1.22 ml of thionyl chloride are added dropwise and the mixture is left stirring for 30 minutes at 0° C. The reaction mixture is washed twice with water, dried over Na$_2$SO$_4$ and concentrated by half under vacuum and this solution is used as is in Preparation 3.10.

Preparation 1.7

3,5-Dichloro-3-(1,3-benzodioxol-4-yl)-1,3-dihydro-2H-indol-2-one (IV): R$_1$=Cl; R$_2$=H; R$_3$+R$_4$=2,3-O—CH$_2$—O—; Hal=Cl A) 4-Bromo-1,3-benzodioxole This compound is prepared according to the process described in Tetrahedron Lett., 1995, 36, 6413–6414.

B) 5-Chloro-3-(1,3-benzodioxol-4-yl)-3-hydroxy-1,3-dihydro-2H-indol-2-one.

A solution of 1,3-benzodioxol-4-ylmagnesium bromide is prepared from 0.85 g of magnesium in 10 ml of THF and from a solution of 6.7 g of the compound obtained in the preceding stage in 40 ml of THF. This solution is added, dropwise and at a temperature of less than 40° C., to a mixture of 3 g of 5-chloro-1H-indole-2,3-dione in 50 ml of THF and then left stirring for one hour. The reaction mixture is poured onto a saturated NH$_4$Cl solution and extracted with AcOEt, the organic phase is washed with water and dried over Na$_2$SO$_4$, and the solvent is evaporated under vacuum. 1.12 g of the expected product are obtained after crystallization from DCM, M.p.=271° C.

C) 3,5-Dichloro-3-(1,3-benzodioxol-4-yl)-1,3-dihydro-2H-indol-2-one.

0.3 ml of thionyl chloride is added, at a temperature of less than 25° C., to a mixture of 1.1 g of the compound obtained in the preceding stage and 0.4 ml of pyridine in 20 ml of DCM and the mixture is left stirring for 30 minutes. The reaction mixture is washed twice with water, the organic phase is dried over Na$_2$SO$_4$ and the solvent is evaporated under vacuum. 0.62 g of the expected product is obtained after crystallization from DCM, M.p.=241° C.

Preparation 1.8

3-Bromo-5,6-dichloro-3-(2-chlorophenyl)-1,3-dihydro-2H-indol-2-one (IV): R$_1$=Cl; R$_2$=6-Cl; R$_3$=Cl; R$_4$=H; Hal=Br This compound is prepared according to the procedures disclosed in WO 95/18105 in stages A), B) and C) of Preparation 72.

Preparation 1.9

3,5-Dichloro-3-(2-chlorophenyl)-6-methoxy-1,3-dihydro-2H-indol-2-one (IV): R$_1$=Cl; R$_2$=6-OCH$_3$; R$_3$=Cl; R$_4$=H; Hal=Cl A) 4–Chloro-3-methoxyaniline.

A mixture of 36 g of 2-chloro-5-nitroanisole and Raney® nickel in 150 ml of MeOH and 200 ml of THF is hydrogenated in a Parr apparatus for 4 hours at 35° C. under a pressure of 1.3 bar. The catalyst is filtered off through Celite® and the filtrate is concentrated under vacuum. 28 g of the expected product are obtained, which product is used as is.

B) N-(4-Chloro-3-methoxyphenyl)-DL-2-chloromandelamide.

A mixture of 28 g of the compound obtained in the preceding stage and 33.13 g of DL-2-chloromandelic acid in 128 ml of 1,2-dichlorobenzene is heated at 230° C. for 4 hours, the water formed being removed using a Dean & Stark apparatus. The reaction mixture is partially concentrated under vacuum and left to crystallize. The crystalline product formed is filtered off and washed with iso ether. 40 g of the expected product are obtained.

C) 5-Chloro-3-(2-chlorophenyl)-6-methoxy-1,3-dihydro-2H-indol-2-one.

40 g of the compound obtained in the preceding stage are rapidly added to 550 g of polyphosphoric acid and then the mixture is heated at 60° C. for 8 hours and left stirring overnight while allowing the temperature to return to AT. Ice-cold water is added to the reaction mixture and the precipitate formed is filtered off and washed with water. The precipitate is taken up in AcOEt and the white product obtained after trituration is filtered off and washed with iso ether. 17.2 g of the expected product are obtained, M.p.=243–247° C.

D) 5-Chloro-3-(2-chlorophenyl)-3-hydroxy-6-methoxy-1,3-dihydro-2H-indol-2-one.

2.56 g of 60% sodium hydride in oil are added at AT, under an argon atmosphere, to a solution of 17.2 g of the compound obtained in the preceding stage in 220 ml of THF. After the evolution of gas has ceased, 6.85 g of dimethyl disulphide are added, air is sparged into the reaction mixture and the mixture is left stirring for 72 hours at AT. Water is added to the reaction mixture, the THF is evaporated under vacuum, the remaining aqueous phase is extracted with AcOEt, the organic phase is washed with water and with a saturated NaCl solution and is dried over $Na_2SO_4$, and the solvent is evaporated under vacuum. The product obtained is dissolved in DCM, the solvent is partially concentrated, crystallization is allowed to take place and the crystalline product formed is filtered off. 6 g of the expected product are obtained, M.p.=237–240° C.

E) 3,5-Dichloro-3-(2-chlorophenyl)-6-methoxy-1,3-dihydro-2H-indol-2-one.

A suspension of 3 g of the compound obtained in the preceding stage in 90 ml of DCM is cooled in an ice bath, 1.2 ml of pyridine and then 0.96 ml of thionyl chloride are added, and the mixture is left stirring for 30 minutes. The reaction mixture is washed with water until the pH is neutral, the organic phase is dried over $Na_2SO_4$ and the solution is concentrated under vacuum by half. A solution of the expected product is obtained, which solution is used directly in Preparation 3.13.

Preparation 1.10

3,6-Dichloro-3-(2-methoxyphenyl)-5-methyl-1,3-dihydro-2H-indol-2-one (IV): $R_1=CH_3$; $R_2=6$-Cl; $R_3=OCH_3$; $R_4=H$; Hal=Cl A) 6-Chloro-5-methyl-3-methylthio-1,3-dihydro-2H-indol-2-one and 4-Chloro-5-methyl-3-methylthio-1,3-dihydro-2H-indol-2-one.

8.5 ml of chlorine are introduced into 320 ml of DCM, cooled to −70° C., then a solution of 24 ml of ethyl methylthioacetate in 60 ml of DCM is added over 20 minutes at −70° C. and the mixture is left stirring for 15 minutes at −70° C. A solution of 52.64 g of 3-chloro-4-methylaniline in 100 ml of DCM is subsequently added at −70° C. over 30 minutes and the mixture is left stirring for 1 hour 45 minutes at −70° C. Finally, 41.3 ml of triethylamine are added at −70° C. and the mixture is left stirring for 1 hour while allowing the temperature to rise to AT. The reaction mixture is washed twice with 250 ml of water, the organic phase is dried over $MgSO_4$ and the solvent is evaporated under vacuum. The residue is taken up in a mixture of 600 ml of ether and 130 ml of 2N HCl and the mixture is left stirring for 72 hours at AT. An insoluble material is filtered off, the filtrate is separated by settling, the organic phase is washed twice with water and dried over $MgSO_4$, and the solvent is evaporated under vacuum. The residue is chromatographed on silica gel, elution being carried out with DCM and then with a DCM/AcOEt (85/15, v/v) mixture. The mixture obtained is rechromatographed on silica gel, elution being carried out with DCM and then with a DCM/AcOEt (95/5, v/v) mixture. The two isomers are separated:

the less polar isomer, which is 6-chloro-5-methyl-3-methylthio-1,3-dihydro-2H-indol-2-one, and 1.16 g are obtained, the more polar isomer, which is 4-chloro-5-methyl-3-methylthio-1,3-dihydro-2H-indol-2-one, and 0.72 g is obtained.

B) 6-Chloro-5-methyl-1H-indole-2,3-dione.

A mixture of 1.16 g of 6-chloro-5-methyl-3-methylthio-1,3-dihydro-2H-indol-2-one, obtained in the preceding stage, and 0.681 g of N-chlorosuccinimide in 100 ml of carbon tetrachloride is heated at reflux for 1 hour. The reaction mixture is concentrated under vacuum and the residue is taken up in a mixture of 80 ml of THF and 20 ml of water and then heated at reflux for 16 hours. The THF is evaporated under vacuum, the remaining aqueous phase is extracted with AcOEt, the organic phase is washed with water and with a saturated NaCl solution and dried over. $Na_2SO_4$ and the solvent is evaporated under vacuum. The residue is chromatographed on silica gel, elution being carried out with DCM and then with the gradient of the DCM/AcOEt mixture up to (85/15, v/v). 0.793 g of the expected product is obtained, M.p.=264° C.

C) 6-Chloro-3-hydroxy-3-(2-methoxyphenyl)-5-methyl-1,3-dihydro-2H-indol-2-one.

A solution of 2-methoxyphenylmagnesium bromide is prepared from 0.687 g of magnesium in 1.5 ml of ether and from a solution of 5.35 g of 1-bromo-2-methoxybenzene in 7.55 ml of ether. This solution is added dropwise, under an argon atmosphere, to a mixture, cooled beforehand in an ice bath, of 1.4 g of the compound obtained in the preceding stage in 14 ml of THF and then the mixture is left stirring while allowing the temperature to rise to AT. After stirring for 1 hour at AT, the reaction mixture is slowly poured onto a saturated $NH_4Cl$ solution, the THF is evaporated under vacuum, extraction is carried out with AcOEt, the organic phase is washed with water and with a saturated NaCl solution and dried over $Na_2SO_4$, and the AcOEt is evaporated under vacuum. The residue is chromatographed on silica gel, elution being carried out with DCM and then with a DCM/MeOH (98/2, v/v) mixture. 1.6 g of the expected product are obtained after crystallization from a THF/MeOH mixture, M.p.=266° C.

D) 3,6-Dichloro-3-(2-methoxyphenyl)-5-methyl-1,3-dihydro-2H-indol-2-one.

A suspension of 0.913 g of the compound obtained in the preceding stage in 10 ml of DCM is cooled in an ice bath, 0.36 ml of pyridine and then 0.33 ml of thionyl chloride are added and the mixture is left stirring for 20 minutes. The reaction mixture is diluted by addition of 50 ml of DCM, the organic phase is washed three times with water and dried over $Na_2SO_4$, and the solvent is evaporated under vacuum. 0.5 g of the expected product is obtained.

Preparation 1.11

3,4-Dichloro-3-(2-methoxyphenyl)-5-methyl-1,3-dihydro-2H-indol-2-one (IV): $R_1$=$CH_3$; $R_2$=4-Cl; $R_3$=$OCH_3$; $R_4$=H; Hal=Cl A) 4-Chloro-5-methyl-1H-indole-2,3-dione This compound is prepared according to the procedure described in stage B of Preparation 1.10 from 0.72 g of 4-chloro-5-methyl-3-methylthio-1,3-dihydro-2H-indol-2-one and 0.422 g of N-chlorosuccinimide in 72 ml of carbon tetrachloride and then from 58 ml of THF and 14 ml of water. The product obtained is chromatographed on silica gel, elution being carried out with DCM and then with the gradient of the DCM/AcOEt mixture up to (90/10, v/v). 0.5 g of the expected product is obtained.

B) 4-Chloro-3-hydroxy-3-(2-methoxyphenyl)-5-methyl-1,3-dihydro-2H-indol-2-one.

A solution of 5 g of 1-bromo-2-methoxybenzene in 7 ml of ether is added dropwise to a suspension of 0.638 g of magnesium in 1.5 ml of ether until the reaction begins and then the addition is continued while maintaining the reflux. At the end of the addition, the mixture is heated at 30° C. for 20 minutes. This solution is added dropwise and under an argon atmosphere to a suspension of 1.3 g of the compound obtained in the preceding stage in 13 ml of THF cooled beforehand in an ice bath and then the mixture is left stirring while allowing the temperature to rise to AT. After 1 hour at AT, the reaction mixture is poured onto a saturated $NH_4Cl$ solution, the THF is evaporated under vacuum, extraction is carried out with AcOEt, the organic phase is washed with water and with a saturated NaCl solution and dried over $Na_2SO_4$, and the solvent is evaporated under vacuum. The residue is chromatographed on silica gel, elution being carried out with DCM and then with a DCM/MeOH (98/2, v/v) mixture. 0.846 g of the expected product is obtained after crystallization from a THF/MeOH mixture, M.p.=262–263° C.

C) 3,4-Dichloro-3-(2-methoxyphenyl)-5-methyl-1,3-dihydro-2H-indol-2-one.

A suspension of 1.5 g of the-compound obtained in the preceding stage in 30 ml of DCM is cooled to 0° C., 0.6 ml of pyridine and then 0.54 ml of thionyl chloride are added and the mixture is left stirring for 45 minutes. The reaction mixture is diluted by addition of 15 ml of DCM, the organic phase is washed three times with water and dried over $MgSO_4$, and the solvent is evaporated under vacuum. 1 g of the expected product is obtained.

Preparations of the Compounds of Formula (V)

Preparation 2.1

(3S)-N,N-Dimethyl-1,2,3,4-tetrahydroisoquinoline-3-carboxamide Hydrochloride

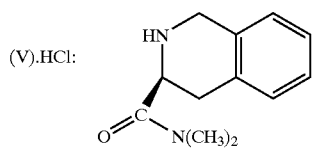

(V).HCl:

A) (3S)-N,N-Dimethyl-2-(tert-butoxycarbonyl)-1,2,3,4-tetrahydroisoquinoline-3-carboxamide.

A solution of 5 g of (3S)-2-(tert-butoxycarbonyl)-1,2,3,4-tetrahydroisoquinoline-3-carboxylic acid (commercial) in 50 ml of DCM is cooled to 0° C. and 5.45 g of triethylamine and then 8 g of BOP are added. Dimethylamine gas is then added by sparging for 5 minutes and the mixture is left stirring for 18 hours at AT. The reaction mixture is taken up in a water/DCM mixture, after separation by settling the organic phase is washed with a 5% $KHSO_4$ solution and with a 5% $Na_2CO_3$ solution and dried over $Na_2SO_4$, and the solvent is evaporated under vacuum. The residue is chromatographed on silica gel, elution being carried out with a DCM/AcOEt (70/30, v/v) mixture. 4 g of the expected product are obtained in the form of an oil, which crystallizes.

B) (3S)-N,N-Dimethyl-1,2,3,4-tetrahydroisoquinoline-3-carboxamide Hydrochloride

A mixture of 4 g of the compound obtained in the preceding stage in 50 ml of a 4N solution of HCl in dioxane is left stirring for 2 hours at AT. The reaction mixture is concentrated under vacuum, the residue is taken up in a DCM/iso ether mixture and the precipitate formed is filtered off. 4.9 g of the expected product are obtained.

Preparation 2.2

(1S)-N,N-Dimethyl-1,2,3,4-tetrahydroisoquinoline-1-carboxamide

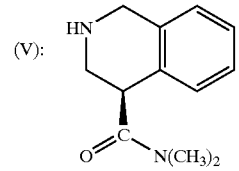

(V):

A) (1S)-N,N-Dimethyl-2-(9-fluorenylmethoxycarbonyl)-1,2,3,4-tetrahydroisoquinoline-1-carboxamide 1.61 g of diisopropylethylamine, 5.53 g of BOP and then 5 ml of a 5.6M solution of dimethylamine in ethanol are added to a solution of 5 g of (1S)-2-(9-fluorenylmethoxycarbonyl)-1,2,3,4-tetrahydroisoquinoline-1-carboxylic acid (commercial) in 100 ml of DCM and the mixture is left stirring for 3 hours at AT. The reaction mixture is taken up in a water/DCM mixture, after separation by settling the organic phase is washed with a 5% $KHSO_4$ solution and dried over $Na_2SO_4$, and the solvent is evaporated under vacuum. The residue is chromatographed on silica gel, elution being carried out with a DCM/AcOEt (70/30, v/v) mixture. 4.5 g of the expected product are obtained in the form of an oil.

B) (1S)-N,N-Dimethyl-1,2,3,4-tetrahydroisoquinoline-1-carboxamide.

This compound is prepared by using the method described in Synthetic Communications, 1994, 24(2), 187–195. 4 g of potassium fluoride and 0.4 g of 18-crown-6 crown ether are added, at AT and under a nitrogen atmosphere, to a solution of 4.5 g of the compound obtained in the preceding stage in 50 ml of DMF and the mixture is left stirring for 18 hours at AT. The reaction mixture is concentrated under vacuum, the residue is taken up in ether, an insoluble material is filtered off and the filtrate is concentrated under vacuum. The resulting oil is chromatographed on silica gel, elution being carried out with a DCM/MeOH (80/20, v/v) mixture. 1.6 g of the expected product are obtained in the form of an oil.

Preparation 2.3

(2S)-N,N-Dimethyl-2,3-dihydro-1H-indole-2-carboxamide

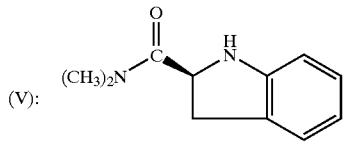

A) (2S)-N,N-Dimethyl-1-(tert-butoxycarbonyl)-2,3-dihydro-1H-indole-2-carboxamide.

A mixture of 5 g of (2S)-1-(tert-butoxycarbonyl)-2,3-dihydro-1H-indole-2-carboxylic acid (commercial) and of 5.8 g of triethylamine in 100 ml of DCM is cooled in an ice bath, 8.4 g of BOP are added and the mixture is left stirring for 15 minutes. Dimethylamine gas is then added by sparging for 10 minutes and the mixture is left stirring for 3 hours at AT. The reaction mixture is concentrated under vacuum, the residue is extracted with AcOEt, the organic phase is washed with water, with a 5% $Na_2CO_3$ solution and with a 5% $KHSO_4$ solution and dried over $Na_2SO_4$, and the solvent is evaporated under vacuum. The residue is chromatographed on silica gel, elution being carried out with a DCM/AcOEt (85/15, v/v) mixture. 4.1, g of the expected product are obtained.

B) (2S)-N,N-Dimethyl-2,3-dihydro-1H-indole-2-carboxamide.

A mixture of 4 g of the compound obtained in the preceding stage in 20 ml of TFA is left stirring for 2 hours at AT. The reaction mixture is concentrated under vacuum, the residue is taken up in a 5% $Na_2CO_3$ solution until a pH of 9 is reached, extraction is carried out with ether, the organic phase is dried over $Na_2SO_4$ and the solvent is evaporated under vacuum. 2.65 g of the expected product are obtained.

Preparation 2.4

Hydrochloride of the Methyl Ester of (3S)-1,2,3,4-Tetrahydroisoquinoline-3-carboxylic Acid

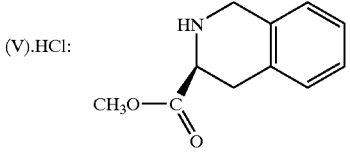

A mixture of 5 g of (3S)-1,2,3,4-tetrahydroisoquinoline-3-carboxylic acid (commercial) and of 100 ml of a saturated solution of hydrochloric acid in MeOH is heated at reflux for 72 hours. The reaction mixture is concentrated under vacuum, the residue is taken up in MeOH and the solvent is evaporated under vacuum. 6 g of the expected product are obtained.

Preparation 2.5

N,N-Dimethylisoindoline-1-carboxamide

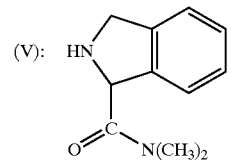

A) N,N-Dimethyl-2-(9-fluorenylmethoxycarbonyl)-isoindoline-1-carboxamide.

1.66 g of DIPEA and then 5.73 g of BOP are added to a solution of 5 g of 2-(9-fluorenylmethoxycarbonyl)isoindoline-1-carboxylic acid (commercial) in 100 ml of DCM and the mixture is left stirring for 15 minutes at AT. 4.6 ml of a 5.6M solution of dimethylamine in EtOH are subsequently added and the mixture is left stirring for 30 minutes at AT. The reaction mixture is concentrated under vacuum, the residue is taken up in water and extracted with DCM, the organic phase is washed with a 5% $KHSO_4$ solution and dried over $Na_2SO_4$, and the solvent is evaporated under vacuum. The residue is chromatographed on silica gel, elution being carried out with a DCM/AcOEt (70/30, v/v) mixture. 5 g of the expected product are obtained.

B) N,N-Dimethylisoindoline-1-carboxamide.

This compound is prepared using the method described in Synthetic Communications, 1994, 24(2), 187–195. 4.6 g of potassium fluoride and 1 g of 18-crown-6 crown ether are added, at AT and under a nitrogen atmosphere, to a solution of 5 g of the compound obtained in the preceding stage in 50 ml of DMF and the mixture is left stirring for 20 hours at AT. The reaction mixture is concentrated under vacuum, the residue is taken up in ether, the insoluble material is filtered off and the filtrate is concentrated under vacuum. The residue is chromatographed on silica gel, elution being carried out with a DCM/MeOH (95/5, v/v) mixture. 1.5 g of the expected product are obtained.

Preparation 2.6

(3S)-N,N-Dimethyl-6,7-dimethoxy-1,2,3,4-tetrahydroisoquinoline-3-carboxamide Hydrochloride

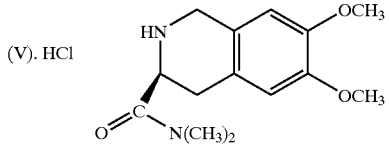

A) (3S)-2-(tert-Butoxycarbonyl)-6,7-dimethoxy-1,2,3,4-tetrahydroquinoline-3-carboxylic Acid.

A mixture of 10 g of (3S)-6,7-dimethoxy-1,2,3,4-tetrahydroquinoline-3-carboxylic acid para-toluenesulphonate (commercial), 5.85 g of di-tert-butyl dicarbonate and 5.17 g of triethylamine in 100 ml of dioxane and 50 ml of water is left stirring for 18 hours. The mixture is concentrated under vacuum, the residue is taken up in water, the aqueous phase is washed with ether, the aqueous phase is acidified to a pH of 3 by addition of $KHSO_4$ and extracted with DCM, the organic phase is dried over $Na_2SO_4$ and the solvent is evaporated under vacuum. 10 g of the expected product are obtained in the form of an oil.

B) (3S)-N,N-Dimethyl-2-(tert-butoxycarbonyl)-6,7-dimethoxy-1,2,3,4-tetrahydroisoquinoline-3-carboxamide.

A solution of 10 g of the compound obtained in the preceding stage and 8.96 g of triethylamine in 200 ml of DCM is cooled in an ice bath, 13 g of BOP are added and the mixture is left stirring for 15 minutes. Dimethylamine gas is then added by sparging for 5 minutes and the mixture is left stirring for 18 hours at AT. The mixture is concentrated under vacuum, the residue is extracted with AcOEt, the organic phase is washed with water, with a 5% $Na_2CO_3$ solution and with a 5% $KHSO_4$ solution and dried over $Na_2SO_4$, and the solvent is evaporated under vacuum. The residue is chromatographed on silica gel, elution being carried out with a DCM/AcOEt (60/40, v/v) mixture. 7.6 g of the expected product are obtained after crystallization from iso ether.

C) (3S)-N,N-Dimethyl-6,7-dimethoxy-1,2,3,4-tetrahydroisoquinoline-3-carboxamide Hydrochloride.

A mixture of 7.6 g of the compound obtained in the preceding stage in 50 ml of a 4N solution of HCl in dioxane is left stirring for 3 hours at AT. The mixture is concentrated under vacuum, the residue is taken up in ether and the precipitate formed is filtered off. 6.2 g of the expected product are obtained.

Preparation of the Compounds of Formula (II)

Preparation 3.1

(3S)-2-[5-Chloro-3-(2-methoxyphenyl)-2-oxo-2,3-dihydro-1H-indol-3-yl]-N,N-dimethyl-1,2,3,4-tetrahydroisoquinoline-3-carboxamide, Mixture of Diastereoisomers (II): $R_1$=Cl; $R_2$=H; $R_3$=$OCH_3$; $R_4$=H; $R_5$=$N(CH_3)_2$;
$R_8$=H; $R_8$=H; n=1; p=1

A mixture of 2 g of the compound obtained in Preparation 1.1, 1.71 g of the compound obtained in Preparation 2.1 and 1.5 g of triethylamine in 50 ml of THF is left stirring for 48 hours at AT. The reaction mixture is concentrated under vacuum, the residue is extracted with DCM, the organic phase is washed with water and dried over $Na_2SO_4$, and the solvent is evaporated under vacuum. The residue is chromatographed on silica gel, elution being carried out with a DCM/AcOEt (50/50, v/v) mixture. 3.6 g of the expected product are obtained in the form of the mixture of diastereoisomers.

Preparation 3.2

(1S)-2-[5-Chloro-3-(2-methoxyphenyl)-2-oxo-2,3-dihydro-1H-indol-3-yl]-N,N-dimethyl-1,2,3,4-tetrahydroisoquinoline-1-carboxamide, Mixture of Diastereoisomers (II): $R_1$=Cl; $R_2$=H; $R_3$=$OCH_3$; $R_4$=H; $R_5$=$N(CH_3)_2$;
$R_8$=H; $R_8$=H; n=2; p=0.

This compound is prepared according to the procedure described in Preparation 3.1 from 2.4 g of the compound obtained in Preparation 1.1, 1.6 g of the compound obtained in Preparation 2.2 and 1.57 g of triethylamine in 50 ml of THF. 2.5 g of the expected product are obtained in the form of the mixture of the diastereoisomers.

Preparation 3.3

(2S)-1-[5-Chloro-3-(2-methoxyphenyl)-2-oxo-2,3-dihydro-1H-indol-3-yl]-N,N-dimethyl-2,3-dihydro-1H-indole-2-carboxamide, Levorotatory Isomer (II): $R_1$=Cl; $R_2$=H; $R_3$=$OCH_3$; $R_4$=H; $R_5$=$N(CH_3)_2$;
$R_8$=H; $R_8$=H; n=0; p=1

A mixture of 5 g of the compound obtained in Preparation 1.1, 3 g of the compound obtained in Preparation 2.3 and 1.62 g of triethylamine in 100 ml of THF and 100 ml chloroform is left stirring for 48 hours at AT. The reaction mixture is concentrated under vacuum, the residue is extracted with DCM, the organic phase is washed with water and dried over $Na_2SO_4$, and the solvent is evaporated under vacuum. The residue is chromatographed on silica gel, elution being carried out with a DCM/AcOEt (50/50, v/v) mixture. The diastereoisomers are separated and the more polar compound is collected. 2.2 g of the expected product are obtained in the form of foams. $\alpha_D^{20}$=−515° (c=0.4, chloroform).

Preparation 3.4

Methyl Ester of (3S)-2-[5-Chloro-3-(2-methoxyphenyl)-2-oxo-2,3-dihydro-1H-indol-3-yl]-1,2,3,4-tetrahydroisoquinoline-3-carboxylic Acid, Mixture of Diastereoisomers (II): $R_1$=Cl; $R_2$=H; $R_3$=$OCH_3$; $R_4$=H; $R_5$=$OCH_3$;
$R_8$=H; $R_8$=H; n=1; p=1

A mixture of 1.6 g of the compound obtained in Preparation 1.1, 1.42 g of the compound obtained in Preparation 2.4 and 1.3 g of triethylamine in 20 ml of THF and 20 ml of chloroform is heated at reflux for 2 hours. The reaction mixture is concentrated under vacuum, the residue is extracted with DCM, the organic phase is washed with water and dried over $Na_2SO_4$, and the solvent is evaporated under vacuum. The residue is chromatographed on silica gel, elution being carried out with DCM and then with the gradient of the DCM/AcOEt mixture from (99/1, v/v) to (90/10, v/v). 2.3 g of the expected product are obtained in the form of the mixture of diastereoisomers.

Preparation 3.5

2-[5-Chloro-3-(2-methoxyphenyl)-2-oxo-2,3-dihydro-1H-indol-3-yl]-N,N-dimethylisoindoline-1-carboxamide (II): $R_1$=Cl; $R_2$=H; $R_3$=$OCH_3$; $R_4$=H; $R_5$=$N(CH_3)_2$;
$R_8$=H; $R_8$=H; n=1; p=0

A mixture of 1.48 g of the compound obtained in Preparation 1.1, 0.91 g of the compound obtained in Preparation 2.5 and 0.5 g of triethylamine in 50 ml of THF is left stirring for 48 hours at AT. The reaction mixture is concentrated under vacuum, the residue is taken up in water and extracted with DCM, the organic phase is dried over $Na_2SO_4$ and the solvent is evaporated under vacuum. 2.5 g of the expected product are obtained in the form of foams, which product is used as is.

Preparation 3.6

(3S)-2-[5,6-Dichloro-3-(2-methoxyphenyl)-2-oxo-2,3-dihydro-1H-indol-3-yl]-N,N-dimethyl-1,2,3,4-tetrahydroisoquinoline-3-carboxamide, Mixture of Diastereoisomers (II): $R_1$=Cl; $R_2$=6-Cl; $R_3$=$OCH_3$; $R_4$=H; $R_5$=N($CH_3$) 2; $R_8$=H; $R_8$=H; n=1; p=1

0.7 g of triethylamine is added to a solution of 1.5 g of the compound obtained in Preparation 1.2 and 1.5 g of the compound obtained in Preparation 2.1 (in the form of a free base) in 30 ml of THF and the mixture is left stirring for 18 hours at AT. The reaction mixture is concentrated under vacuum, the residue is extracted with DCM, the organic phase is washed with water and dried over $Na_2SO_4$, and the solvent is evaporated under vacuum. The residue is chromatographed on silica gel, elution being carried out with a DCM/AcOEt (60/40, v/v) mixture. 1.4 g of the expected product are obtained in the form of the mixture of diastereoisomers.

Preparation 3.7

(3S)-2-[5-Chloro-3-(2-methoxyphenyl)-6-methyl-2-oxo-2,3-dihydro-1H-indol-3-yl]-N,N-dimethyl-1,2,3,4-tetrahydroisoquinoline-3-carboxamide, Mixture of Diastereoisomers (II): $R_1$=Cl; $R_2$=6-$CH_3$; $R_3$=$OCH_3$; $R_4$=H; $R_5$=N($CH_3$)$_2$; $R_8$=H; $R_8$=H; n=1; p=1

1.7 g of the compound obtained in Preparation 2.1 (in the form of the free base) and then 0.86 g of triethylamine are added to a solution of the compound obtained in Preparation 1.3 in 50 ml of THF and the mixture is left stirring for 18 hours at AT. The reaction mixture is concentrated under vacuum, the residue is extracted with AcOEt, the organic phase is washed with water and dried over $Na_2SO_4$, and the solvent is evaporated under vacuum. The residue is chromatographed on silica gel, elution being carried out with a DCM/AcOEt (50/50, v/v) mixture. 1.5 g of the expected product are obtained in the form of the mixture of diastereoisomers.

Preparation 3.8

(3S)-2-[5-Chloro-3-(2-chlorophenyl)-2-oxo-2,3-dihydro-1H-indol-3-yl]-N,N-dimethyl-1,2,3,4-tetrahydroisoquinoline-3-carboxamide, Mixture of Diastereoisomers (II): $R_1$=Cl; $R_2$=H; $R_3$=Cl; $R_4$=H; $R_5$=N($CH_3$)$_2$; $R_8$=H; $R_8$=H; n=1; p=1

A mixture of 2 g of the compound obtained in Preparation 1.4, 1.25 g of the compound obtained in Preparation 2.1 (free base) and 0.678 g of triethylamine in 50 ml of THF is left stirring for 3 hours at AT. The reaction mixture is concentrated under vacuum, the residue is extracted with DCM, the organic phase is washed with water and dried over $Na_2SO_4$, and the solvent is evaporated under vacuum. The residue is chromatographed on silica gel, elution being carried out with a DCM/AcOEt (80/20, v/v) mixture. 1.7 g of the expected product are obtained in the form of the mixture of the diastereoisomers.

Preparation 3.9

(3S)-2-[5-Chloro-3-(2,3-dimethoxyphenyl)-2-oxo-2,3-dihydro-1H-indol-3-yl]-N,N-dimethyl-1,2,3,4-tetrahydroisoquinoline-3-carboxamide, Mixture of Diastereoisomers (II): $R_1$=Cl; $R_2$=H; $R_3$=$OCH_3$; $R_4$=3-$OCH_3$; $R_5$=N($CH_3$)$_2$; $R_8$=H; $R_8$=H; n=1; p=1

2.63 g of triethylamine are added to a mixture of the compound obtained in Preparation 1.5 and 1.7 g of the compound obtained in Preparation 2.1 in 50 ml of THF and 10 ml of DCM and the mixture is left stirring for 72 hours at AT. The mixture is concentrated under vacuum, the residue is extracted with DCM, the organic phase is washed with water and dried over $Na_2SO_4$, and the solvent is evaporated under vacuum. The residue is chromatographed on silica gel, elution being carried out with a DCM/AcOEt (50/50, v/v) mixture. 1.2 g of the expected product are obtained in the form of the mixture of diastereoisomers.

Preparation 3.10

(3S)-2-[5-Chloro-3-(2,4-dimethoxyphenyl)-2-oxo-2,3-dihydro-1H-indol-3-yl]-N,N-dimethyl-1,2,3,4-tetrahydroisoquinoline-3-carboxamide, Mixture of Diastereoisomers (II): $R_1$=Cl; $R_2$=H; $R_3$=$OCH_3$; $R_4$=4-$OCH_3$; $R_5$=N($CH_3$)$_2$; $R_8$=H; $R_9$=H; n=1; p=1

3 g of the compound obtained in Preparation 2.1 (free base) and 1.6 g of triethylamine are added to the solution of the compound obtained in Preparation 1.6 in DCM and then the mixture is left stirring for 18 hours at AT. The reaction mixture is diluted by addition of DCM, the organic phase is washed with water and dried over $Na_2SO_4$, and the solvent is evaporated under vacuum. The residue is chromatographed on silica gel, elution being carried out with a DCM/AcOEt (50/50, v/v) mixture. 2.8 g of the expected product are obtained in the form of the mixture of diastereoisomers.

Preparation 3.11

(3S)-2-[5-Chloro-3-(1,3-benzodioxol-4-yl)-2-oxo-2,3-dihydro-1H-indol-3-yl]-N,N-dimethyl-1,2,3,4-tetrahydroisoquinoline-3-carboxamide, Mixture of Diastereoisomers (II): $R_1$=Cl; $R_2$=H; $R_3$+$R_4$=2,3-O—$CH_2$—O—; $R_5$=N($CH_3$)$_2$; $R_8$=H; $R_8$=H; n=1; p=1

0.89 g of the compound obtained in Preparation 2.1 (free base), and then 0.52 g of triethylamine are added to a solution of 1.5 g of the compound obtained in Preparation 1.7 in 15 ml of THF and the mixture is left stirring for 18 hours at AT. The mixture is concentrated under vacuum, the residue is extracted with DCM, the organic phase is washed with water and dried over $Na_2SO_4$, and the solvent is evaporated under vacuum. The residue is chromatographed on silica gel, elution being carried out with a DCM/AcOEt (70/30, v/v) mixture. 1.5 g of the expected product are obtained in the form of the mixture of diastereoisomers.

Preparation 3.12

(3S)-2-[5,6-Dichloro-3-(2-chlorophenyl)-2-oxo-2,3-dihydro-1H-indol-3-yl]-N,N-dimethyl-1,2,3,4-tetrahydroisoquinoline-3-carboxamide, Mixture of Diastereoisomers (II): $R_1$=Cl; $R_2$=6-Cl; $R_3$=Cl; $R_4$=H; $R_5$=N($CH_3$)$_2$; $R_8$=H; $R_8$=H; n=1; p=1

A mixture of 2.66 g of the compound obtained in Preparation 1.8, 2.1 g of the compound obtained in Preparation 2.1 (free base) and 1 g of triethylamine in 100 ml of DCM is left stirring for 18 hours at AT. The reaction mixture is washed with water, the organic phase is dried over $Na_2SO_4$ and the solvent is evaporated under vacuum. The residue is chromatographed on silica gel, elution being carried out with a DCM/AcOEt (80/20, v/v) mixture. 1.1 g of the expected product are obtained in the form of the mixture of diastereoisomers.

Preparation 3.13

(3S)-2-[5-Chloro-3-(2-chlorophenyl)-6-methoxy-2-oxo-2,3-dihydro-1H-indol-3-yl]-N,N-dimethyl-1,2,3,4-tetrahydroisoquinoline-3-carboxamide, Mixture of Diastereoisomers (II): $R_1$=Cl; $R_2$=6-$OCH_3$; $R_3$=Cl; $R_4$=H; $R_5$ N($CH_3$)$_2$; $R_8$=H; $R_8$=H; n=1; p=1

2.26 g of the compound obtained in Preparation 2.1 (free base) and 1.4 g of triethylamine are added to the solution of the compound obtained in Preparation 1.9 in DCM and the mixture is left stirring for 18 hours at AT. The reaction mixture is diluted with DCM, the organic phase is washed with water and dried over $Na_2SO_4$, and the solvent is evaporated under vacuum. The residue is chromatographed on silica gel, elution being carried out with a DCM/AcOEt (50/50, v/v) mixture. 1.3 g of the expected product are obtained in the form of the mixture of diastereoisomers.

Preparation 3.14

(3S)-2-[4-Chloro-3-(2-methoxyphenyl)-5-methyl-2-oxo-2,3-dihydro-1H-indol-3-yl]-N,N-dimethyl-1,2,3,4-tetrahydroisoquinoline-3-carboxamide, Mixture of Diastereoisomers (II): $R_1=CH_3$; $R_2$=4-Cl; $R_3=OCH_3$; $R_4$=H; $R_5$=N$(CH_3)_2$; $R_8$=H; $R_8$=H; n=1; p=1

1.5 g of the compound obtained in Preparation 2.1 (free base) and 1 g of triethylamine are added to a solution of 1 g of the compound obtained in Preparation 1.11 in 50 ml of THF and the mixture is heated at reflux for 18 hours. The reaction mixture is concentrated under vacuum, the residue is extracted with DCM, the organic phase is washed with water and dried over $Na_2SO_4$, and the solvent is evaporated under vacuum. The residue is chromatographed on silica gel, elution being carried out with a DCM/AcOEt (50/50, v/v) mixture. 2 g of the expected product are obtained in the form of the mixture of diastereoisomers.

Preparation 3.15

(3S)-2-[5-Chloro-3-(2-methoxyphenyl)-2-oxo-2,3-dihydro-1H-indol-3-yl]-6,7-dimethoxy-N,N-dimethyl-1,2,3,4-tetrahydroisoquinoline-3-carboxamide, Mixture of Diastereoisomers (II): $R_1$=Cl; $R_2$=H; $R_3=OCH_3$; $R_4$=H; $R_5=N(CH_3)_2$; $R_8$=6-$OCH_3$; $R_8$=7-$OCH_3$; n=1; p=1

A mixture of 2 g of the compound obtained in Preparation 1.1, 2.92 g of the compound obtained in Preparation 2.6 and 1.63 g of triethylamine in 100 ml of THF and 25 ml of DCM is heated at reflux for 8 hours. The mixture is concentrated under vacuum, the residue is taken up in water and extracted with DCM, the organic phase is dried over $Na_2SO_4$ and the solvent is evaporated under vacuum. The residue is chromatographed on silica gel, elution being carried out with AcOEt. 3 g of the expected product are obtained in the form of the mixture of diastereoisomers.

Example 1 and 2

(3S)-2-[5-Chloro-1-[(2,4-dimethoxyphenyl)sulphonyl]-3-(2-methoxyphenyl)-2-oxo-2,3-dihydro-1H-indol-3-yl]-N,N-dimethyl-1,2,3,4-tetrahydroisoquinoline-3-carboxamide, Isomer A and Isomer B (I): $R_1$=Cl; $R_2$=H; $R_3=OCH_3$; $R_4$=H; $R_5=N(CH_3)_2$; $R_6$=2-$OCH_3$; $R_7$=$OCH_3$; $R_8$=H; $R_8$=H; n=1; p=1

0.123 g of 60% sodium hydride in oil is added, at AT and under a nitrogen atmosphere, to a solution of 1.4 g of the compound obtained in Preparation 3.1 in 20 ml of DMF and the mixture is left stirring for 15 minutes. 0.7 g of 2,4-dimethoxybenzenesulphonyl chloride is subsequently added and the mixture is left stirring for 3 hours at AT. The reaction mixture is poured into water and extracted with AcOEt, the organic phase is dried over $Na_2SO_4$ and the solvent is evaporated under vacuum. The residue is chromatographed on silica gel, elution being carried out with a DCM/AcOEt (90/10, v/v) mixture. The diastereoisomers are separated:

the less polar, isomer A: compound of Example 1 which crystallizes from heptane, M.p.=186° C. $\alpha_D^{20}$=+138° (c=0.6, chloroform).

the more polar, isomer B: compound of Example 2 which crystallizes from heptane and 0.84 g is obtained, M.p.=160° C. $\alpha_D^{20}$=−263° (c=0.22, chloroform).

$^1$H NMR: $d_6$-DMSO: δ (ppm): 2.4: bs: 6H; 2.9: mt: 2H; 3.1: s: 3H; 3.6 and 3.8: 2bs: 6H; 3.5 and 3.8: 2 mt: 2H; 3.7: d: 1H; 6.5: s: 1H; 6.7: dd: 1H; 6.8 to 7.1: m: 7H; 7.3: mt: 1H; 7.4: dd: 1H; 7.6: d: 1H; 7.8: d: 1H; 8.0: d: 1H.

Example 3

(1S)-2-[5-Chloro-1-[(2,4-dimethoxyphenyl)sulphonyl]-3-(2-methoxyphenyl)-2-oxo-2,3-dihydro-1H-indol-3-yl]-N,N-dimethyl-1,2,3,4-tetrahydroisoquinoline-1-carboxamide, Levorotatory Isomer (I): $R_1$=Cl; $R_2$=H; $R_3=OCH_3$; $R_4$=H; $R_5=N(CH_3)_2$; $R_6$=2-$OCH_3$; $R_7$=$OCH_3$; $R_8$=H; $R_8$=H; n=2; p=0

0.225 g of 60% sodium hydride in oil is added, at AT and under a nitrogen atmosphere, to a solution of 2.5 g of the compound obtained in Preparation 3.2 in 20 ml of DMF and the mixture is left stirring for 30 minutes. 1.25 g of 2,4-dimethoxybenzenesulphonyl chloride are subsequently added and the mixture is left stirring for 1 hour. The reaction mixture is poured into water and extracted with AcOEt, the organic phase is washed with water and dried over $Na_2SO_4$, and the solvent is evaporated under vacuum. The residue is chromatographed on silica gel, elution being carried out with a DCM/AcOEt (90/10, v/v) mixture. The diastereoisomers are separated and the more polar compound is collected. 1.2 g of the expected product are obtained after crystallization from iso ether, M.p.=263° C. $\alpha_D^{20}$=−262° (c=0.4, chloroform).

$^1$H NMR: $d_6$-DMSO: δ (ppm): 2.0 to 3.0: m+2s: 8H; 3.2 to 4.2: mt+s: 11H; 5.2 and 5.4: 2s: 1H; 6.4 to 8.0: mt: 14H.

Example 4

(2S)-1-[5-Chloro-1-[(2,4-dimethoxyphenyl)sulphonyl]-3-(2-methoxyphenyl)-2-oxo-2,3-dihydro-1H-indol-3-yl]-N,N-dimethyl-2,3-dihydro-1H-indole-2-carboxamide, Levorotatory Isomer (I): $R_1$=Cl; $R_2$=H; $R_3=OCH_3$; $R_4$=H; $R_5=N(CH_3)_2$; $R_6$=2-$OCH_3$; $R_7$=$OCH_3$; $R_8$=H; $R_8$=H; n=0; p=1

0.066 g of 60% sodium hydride in oil is added, at AT and under a nitrogen atmosphere, to a solution of 0.7 g of the compound obtained in Preparation 3.3 in 20 ml of DMF and the mixture is left stirring for 15 minutes. 0.36 g of 2,4-dimethoxybenzenesulphonyl chloride is subsequently added and the mixture is left stirring for 2 hours at AT. The reaction mixture is poured into water and extracted with AcOEt, the organic phase is washed with water and dried over $Na_2SO_4$, and the solvent is evaporated under vacuum. The residue is chromatographed on silica gel, elution being carried out with a DCM/AcOEt (70/30, v/v) mixture. 0.58 g of the expected product is obtained after crystallizing from ether, M.p.=167° C. $\alpha_D^{20}$=−305° (c=0.18, chloroform).

$^1$H NMR: $d_6$-DMSO: δ (ppm): 2.4 and 2.7: 2s: 6H; 2.6 and 3.6: 2mt: 2H; 3.1: s: 3H; 3.8: 2s: 6H; 5.2: dd: 1H; 6.4: d: 1H; 6.5: t: 1H; 6.5 to 7.6: m: 10H; 7.8: d: 1H; 8.0: d: 1H.

Example 5

Methyl Ester of (3S)-2-[5-Chloro-1-[(2,4-dimethoxyphenyl)sulphonyl]-3-(2-methoxyphenyl)-2-oxo-2,3-dihydro-1H-indol-3-yl]-1,2,3,4-tetrahydroisoquinoline-3-carboxylic Acid, Levorotatory Isomer (I): $R_1$=Cl; $R_2$H; $R_3$=OCH$_3$; $R_4$=H; $R_5$=OCH$_3$; $R_6$=2-OCH$_3$; $R_7$=OCH$_3$; $R_8$=H; $R_9$=H; n=1; p=1

0.208 g of 60% sodium hydride in oil is added, at AT and under a nitrogen atmosphere, to a solution of 2.3 g of the compound obtained in Preparation 3.4 in 20 ml of DMF and the mixture is left stirring for-15 minutes. 1.17 g of 2,4-dimethoxybenzenesulphonyl chloride are subsequently added and the mixture is left stirring for 2 hours at AT. The reaction mixture is poured into water and extracted with AcOEt, the organic phase is washed with water and dried over Na$_2$SO$_4$, and the solvent is evaporated under vacuum. The residue is chromatographed on silica gel, elution being carried out with a DCM/hexane (70/30, v/v) mixture and then with a DCM/AcOEt (95/5, v/v) mixture. The diastereoisomers are separated and the more polar compound is collected. 1.1 g of the expected product are obtained after crystallization from hexane, M.p.=170° C. $\alpha_D^{20}$=−220° (c=0.2, chloroform).

$^1$H NMR: d$_6$-DMSO: δ (ppm): 2.8 to 4.4: m: 17H; 6.0 to 7.0: m: 9H; 7.2: t: 1H; 7.4: dd: 1H; 7.6: d: 1H; 7.8: d: 1H; 8.0: d: 1H.

Example 6

2-[5-Chloro-1-[(2,4-dimethoxyphenyl)sulphonyl]-3-(2-methoxyphenyl)-2-oxo-2,3-dihydro-1H-indol-3-yl]-N,N-dimethylisoindoline-1-carboxamide (I): $R_1$=Cl; $R_2$=H; $R_3$=OCH$_3$; $R_4$=H; $R_5$=N(CH$_3$)$_2$; $R_6$=2-OCH$_3$; $R_7$=OCH$_3$; $R_8$=H; $R_8$=H; n=1; p=0

0.227 g of 60% sodium hydride in oil is added, at AT and under a nitrogen atmosphere, to a solution of 2.5 g of the compound obtained in Preparation 3.5 in 20 ml of DMF and the mixture is left stirring for 15 minutes at AT. 1.27 g of 2,4-dimethoxybenzenesulphonyl chloride are subsequently added and the mixture is left stirring for 30 minutes at AT. The reaction mixture is poured into water and extracted with AcOEt, the organic phase is washed with water and dried over Na$_2$SO$_4$, and the solvent is evaporated under vacuum. The residue is chromatographed on silica gel, elution being carried with a DCM/AcOEt (90/10, v/v) mixture. The two pairs of enantiomers are separated and the more polar mixture of enantiomers is collected. 0.81 g of the expected product is obtained after crystallization from an iso ether/hexane mixture, M.p.=168° C.

1H NMR: d$_6$-DMSO: δ (ppm): 2.6: s: 6H; 3.3: s: 3H; 3.7: s: 3H; 3.8: s: 3H; 3.9 and 4.2: 2dd: 2H; 5.9: d: 1H; 6.5: dd: 1H; 6.6: d: 1H; 6.9: mt: 2H; 7.1: mt: 2H; 7.2: t: 1H; 7.3: dd: 1H; 7.4: d: 1H; 7.8: 2d: 2H.

Example 7

(3S)-2-[5,6-Dichloro-1-[(2,4-dimethoxyphenyl)sulphonyl]-3-(2-methoxyphenyl)-2-oxo-2,3-dihydro-1H-indol-3-yl]-N,N-dimethyl-1,2,3,4-tetrahydroisoquinoline-3-carboxamide, Levorotatory Isomer (I): $R_1$=Cl; $R_2$=6-Cl; $R_3$=OCH$_3$; $R_4$=H; $R_5$=N(CH$_3$)$_2$; $R_6$=2-OCH$_3$; $R_7$=OCH$_3$; $R_8$=H; $R_8$=H; n=1; p=1

0.111 g of 60% sodium hydride in oil is added, at AT and under a nitrogen atmosphere, to a solution of 1.35 g of the compound obtained in Preparation 3.6 in 10 ml of DMF and the mixture is left stirring for 15 minutes. 0.624 g of 2,4-dimethoxybenzenesulphonyl chloride is subsequently added and the mixture is left stirring for 2 hours at AT. The reaction mixture is poured into water and extracted with AcOEt, the organic phase is dried over Na$_2$SO$_4$ and the solvent is evaporated under vacuum. The residue is chromatographed on silica gel, elution being carried out with a DCM/AcOEt (90/10, v/v) mixture. The diastereoisomers are separated and the more polar compound is collected. 0.8 g of the expected product is obtained after crystallization from heptane, M.p.=155° C. $\alpha_D^{20}$=−221° (c=0.23, chloroform).

$^1$H NMR: d$_6$-DMSO: δ (ppm): 2.0 to 2.6: 2bs: 8H; 2.8: bs: 3H; 3.0 to 5.0: m: 9H; 6.0 to 7.2: m: 1OH; 7.4: d: 1H; 8.0: mt: 2H.

Example 8

(3S)-2-[5-Chloro-1-[(2,4-dimethoxyphenyl)sulphonyl]-3-(2-methoxyphenyl)-6-methyl-2-oxo-2,3-dihydro-1H-indol-3-yl]-N,N-dimethyl-1,2,3,4-tetrahydroisoquinoline-3-carboxamide, Levorotatory Isomer (I): $R_1$=Cl; $R_2$=6-CH$_3$; $R_3$=OCH$_3$; $R_4$=H; $R_5$s=N(CH$_3$)$_2$; $R_6$=2-OCH$_3$; $R_7$=OCH$_3$; $R_8$=H; $R_8$=H; n=1; p=1

This compound is prepared according to the procedure described in Example 1 from 1.4 g of the compound obtained in Preparation 3.7 in 15 ml of DMF, 0.123 g of 60% sodium hydride in oil and 0.7 g of 2,4-dimethoxybenzenesulphonyl chloride. After chromatography on silica gel, elution being carried out with a DCM/AcOEt (90/10, v/v) mixture, the diastereoisomers are separated and the more polar compound is collected. 0.88 g of the expected product is obtained after crystallization from hexane, M.p.=160° C. $\alpha_D^{20}$=−227° (c=0.18, chloroform).

$^1$H NMR: d$_6$-DMSO: δ (ppm): 2.2 to 2.8: m: 11H; 3.6: s: 3H; 3.8: d: 2H; 4.4: bs: 1H; 6.5 to 7.4: mt: 9H; 7.6: dd: 1H; 10.2: 2s: 1H.

Example 9

(3S)-2-[5-Chloro-1-[(2,4-dimethoxyphenyl)sulphonyl]-3-(2-methoxyphenyl)-2-oxo-2,3-dihydro-1H-indol-3-yl]-6,7-dimethoxy-N,N-dimethyl-1,2,3,4-tetrahydroisoquinoline-3-carboxamide, Levorotatory Isomer (I): $R_1$=Cl; $R_2$=H; $R_3$=OCH$_3$; $R_4$=H; $R_5$=N(CH$_3$)$_2$; $R_6$=2-OCH$_3$; $R_7$=OCH$_3$; $R_8$=6-OCH$_3$; $R_8$=7-OCH$_3$; n=1; p=1

This compound is prepared according to the procedure described in Example 1 from 3 g of the compound obtained in Preparation 3.15 in 20 ml of DMF, 0.235 g of 60% sodium hydride in oil and 1.32 g of 2,4-dimethoxybenzenesulphonyl chloride. After chromatography on silica gel, elution being carried out with a DCM/AcOEt (85/15, v/v) mixture, the diastereoisomers are separated and the more polar compound is collected. 0.64 g of the expected product is obtained after crystallization from ether, M.p.=157° C. $\alpha_D^{20}$=−253° (c=0.18, chloroform).

By carrying out the preparations according to the procedures described in the above examples, the compounds according to the invention collated in TABLE I below are prepared from the compounds of formula (II) described in Preparations 3 and 2,4-dimethoxybenzenesulphonyl chloride:

TABLE I

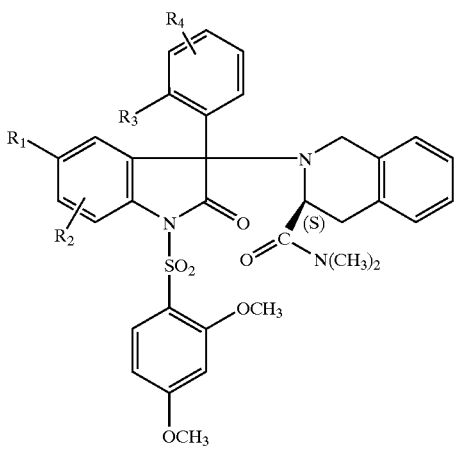

(1): $R_8 = H$; $R_9 = H$;
n = 1; p = 1.

| Examples | $R_1$ | $R_2$ | $R_3$ | $R_4$ | M.p. (° C.); crystallization solvent; $\alpha_D^{20}$ (chloroform) |
|---|---|---|---|---|---|
| 10 (a) | Cl | H | Cl | H | 155 heptane −254° (c = 0.18) |
| 11 (b) | Cl | H | OCH$_3$ | 3-OCH$_3$ | 215 iso ether −275° (c = 0.14) |
| 12 (c) | Cl | H | OCH$_3$ | 4-OCH$_3$ | 145 heptane/ether −252° (c = 0.3) |
| 13 (d) | Cl | H | 2,3-O—CH$_2$—O— | | 160 hexane −233° (c = 0.25) |
| 14 (e) | Cl | 6-Cl | Cl | H | 234 heptane/iso ether −334° (c = 0.22) |
| 15 (f) | Cl | 6-OCH$_3$ | Cl | H | 178 heptane −323° (c = 0.19) |
| 16 (g) | CH$_3$ | 4-Cl | OCH$_3$ | H | 146 iso ether −282° (c = 0.28) |

(a) Compound prepared according to the procedure described in Example 1 from the compound obtained in Preparation 3.8. The reaction product is chromatographed on silica gel, elution being carried out with a DCM/AcOEt (94/6, v/v) mixture and the more polar compound is collected.

(b) Compound prepared according to the procedure described in Example 1 from the compound obtained in Preparation 3.9. The reaction product is chromatographed on silica gel, elution being carried out with a DCM/AcOEt (90/10, v/v) mixture and the more polar compound is collected.

(c) Compound prepared according to the procedure described in Example 1 from the compound obtained in Preparation 3.10. The reaction product is. chromatographed on silica gel, elution being carried out with a DCM/AcOEt (85/15, v/v) mixture and the more polar compound is collected.

(d) Compound prepared according to the procedure described in Example 1 from the compound obtained in Preparation 3.11. The reaction product is chromatographed on silica gel, elution being carried out with a DCM/AcOEt (93/7, v/v) mixture and the more polar compound is collected.

(e) Compound prepared according to the procedure described in Example 1 from the compound obtained in Preparation 3.12. The reaction product is chromatographed on silica gel, elution being carried out with a DCM/AcOEt (90/10, v/v) mixture and the more polar compound is collected.

(f) Compound prepared according to the procedure described in Example 1 from the compound obtained in Preparation 3.13. The reaction product is chromatographed on silica gel, elution being carried out with a DCM/AcOEt (90/10, v/v) mixture and the more polar compound is collected.

(g) Compound prepared according to the procedure described in Example 1 from the compound obtained in Preparation 3.14. The reaction product is chromatographed on silica gel, elution being carried out with a DCM/AcOEt (85/15, v/v) mixture and the more polar compound is collected.

What is claimed is:

1. A compound of formula:

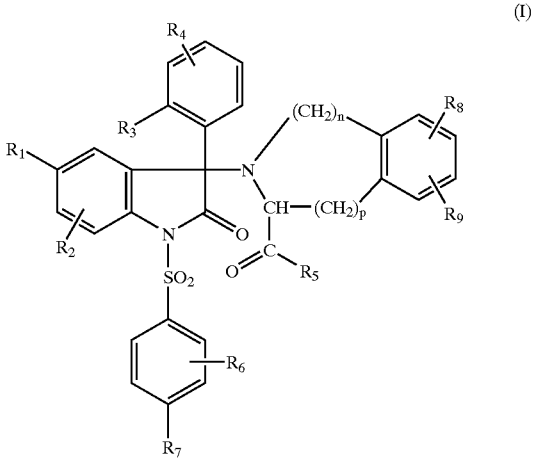

in which:

n is 0, 1 or 2 and p is 0, 1 or 2; the sum n+p being equal to 1 or 2;

$R_1$ represents a halogen atom; a $(C_1-C_4)$alkyl; a $(C_1-C_4)$alkoxy; a trifluoromethyl radical; or a trifluoromethoxy radical;

$R_2$ represents a hydrogen atom; a halogen atom; a $(C_1-C_4)$alkyl; a $(C_1-C_4)$alkoxy; or a trifluoromethyl radical;

or else $R_2$ is in the 6-position of the indol-2-one ring and $R_1$ and $R_2$ together represent the bivalent trimethylene radical;

$R_3$ represents a halogen atom; a hydroxyl; a $(C_1-C_2)$alkyl; a $(C_1-C_2)$alkoxy; or a trifluoromethoxy radical;

$R_4$ represents a hydrogen atom; a halogen atom; a $(C_1-C_2)$alkyl; or a $(C_1-C_2)$alkoxy;

or else $R_4$ is in the 3-position of the phenyl and $R_3$ and $R_4$ together represent the methylenedioxy radical;

$R_5$ represents an ethylamino group; a dimethylamino group; an azetidin-1-yl radical; or a $(C_1-C_2)$alkoxy;

$R_6$ represents a $(C_1-C_4)$alkoxy;

$R_7$ represents a $(C_1-C_4)$alkoxy;

R₈ represents a hydrogen atom; a halogen atom; a (C₁–C₄)alkyl; or a (C₁–C₄)alkoxy; and R₉ represents a hydrogen atom; a halogen atom; a (C₁–C₄)alkyl; or a (C₁–C₄)alkoxy; or a solvate or hydrate thereof.

2. A compound according to claim 1, in the form of optically pure isomers.

3. A compound according to claim 1, of formula:

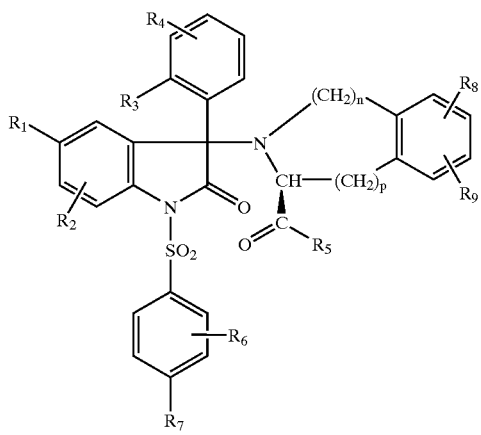

(Ia)

in which:

the carbon atom carrying the COR₅ substituent has the (S) configuration and the carbon atom in the 3-position of the indol-2-one has either the (R) configuration or the (S) configuration.

4. A compound according to claim 3, in the form of the levorotatory isomer.

5. A compound according to claim 4 in which:

the

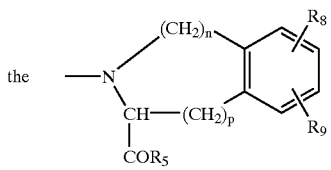

radical represents a radical:

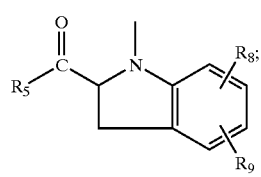

(A)

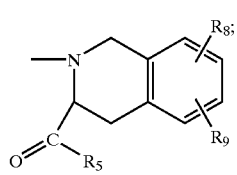

(D)

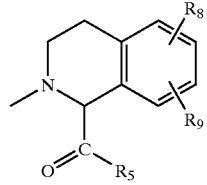

(E)

R₁ represents a chlorine atom or a methyl radical;

R₂ represents a hydrogen atom or is in the 4- or 6-position of the indol-2-one and represents a chlorine atom, a methyl radical or a methoxy radical;

R₃ represents a methoxy radical or a chlorine atom;

R₄ represents a hydrogen atom or is in the 3- or 4-position of the phenyl and represents a methoxy radical;

or else R₄ is in the 3-position of the phenyl and together with R₃ represent a methylenedioxy radical;

R₅ represents a dimethylamino group or a methoxy radical;

R₆ is in the 2-position of the phenyl and represents a methoxy radical;

R₇ represents a methoxy radical; and

R₈ and R₉ represent a hydrogen atom.

6. A compound according to claim 5 chosen from:

(3S)-2-[5-Chloro-1-[(2,4-dimethoxyphenyl)sulphonyl]-3-(2-methoxyphenyl)-2-oxo-2,3-dihydro-1H-indol-3-yl]-N,N-dimethyl-1,2,3,4-tetrahydroisoquinoline-3-carboxamide, levorotatory isomer;

(1S)-2-[5-Chloro-1-[(2,4-dimethoxyphenyl)sulphonyl]-3-(2-methoxyphenyl)-2-oxo-2,3-dihydro-1H-indol-3-yl]-N,N-dimethyl-1,2,3,4-tetrahydroisoquinoline-1-carboxamide, levorotatory isomer;

(2S)-1-[5-Chloro-1-[(2,4-dimethoxyphenyl)sulphonyl]-3-(2-methoxyphenyl)-2-oxo-2,3-dihydro-1H-indol-3-yl]-N,N-dimethyl-2,3-dihydro-1-H-indole-2-carboxamide, levorotatory isomer;

Methyl ester of (3S)-2-[5-chloro-1-[(2,4-dimethoxyphenyl)sulphonyl]-3-(2-methoxyphenyl)-2-oxo-2,3-dihydro-1H-indol-3-yl]-1,2,3,4-tetrahydroisoquinoline-3-carboxylic acid, levorotatory isomer;

(3S)-2-[5,6-Dichloro-1-[(2,4-dimethoxyphenyl)sulphonyl]-3-(2-methoxyphenyl)-2-oxo-2,3-dihydro-1H-indol-3-yl]-N,N-dimethyl-1,2,3,4-tetrahydroisoquinoline-3-carboxamide, levorotatory isomer;

(3S)-2-[5-Chloro-1-[(2,4-dimethoxyphenyl)sulphonyl]-3-(2-methoxyphenyl)-6-methyl-2-oxo-2,3-dihydro-1H-indol-3-yl]-N,N-dimethyl-1,2,3,4-tetrahydroisoquinoline-3-carboxamide, levorotatory isomer;

(3S)-2-[5-Chloro-1-[(2,4-dimethoxyphenyl)sulphonyl]-3-(2-methoxyphenyl)-2-oxo-2,3-dihydro-1H-indol-3-yl]-6,7-dimethoxy-N,N-dimethyl-1,2,3,4-tetrahydroisoquinoline-3-carboxamide, levorotatory isomer;

(3S)-2-[5-Chloro-3-(2-chlorophenyl)-1-[(2,4-dimethoxyphenyl)sulphonyl]-2-oxo-2,3-dihydro-1H-indol-3-yl]-N,N-dimethyl-1,2,3,4-tetrahydroisoquinoline-3-carboxamide, levorotatory isomer;

(3S)-2-[5-Chloro-1-[(2,4-dimethoxyphenyl)sulphonyl]-3-(2,3-dimethoxyphenyl)-2-oxo-2,3-dihydro-1H- indol-3-yl]-N,N-dimethyl-1,2,3,4-tetrahydroisoquinoline-3-carboxamide, levorotatory isomer;

(3S)-2-[5-Chloro-1-[(2,4-dimethoxyphenyl)sulphonyl]-3-(2,4-dimethoxyphenyl)-2-oxo-2,3-dihydro-1H-indol-3-yl]-N,N-dimethyl-1,2,3,4-tetrahydroisoquinoline-3-carboxamide, levorotatory isomer;

(3S)-2-[5-Chloro-3-(1,3-benzodioxol4-yl)-1-[(2,4-dimethoxyphenyl)sulphonyl]-2-oxo-2,3-dihydro-1H-indol-3-yl]-N,N-dimethyl-1,2,3,4-tetrahydroisoquinoline-3-carboxamide, levorotatory isomer;

(3S)-2-[5,6-Dichloro-3-(2-chlorophenyl)-1-[(2,4-dimethoxyphenyl)sulphonyl]-2-oxo-2,3-dihydro-1H-indol-3-yl]-N,N-dimethyl-1,2,3,4-tetrahydroisoquinoline-3-carboxamide, levorotatory isomer;

(3S)-2-[5-Chloro-3-(2-chlorophenyl)-1-[(2,4-dimethoxyphenyl)sulphonyl]-6-methoxy-2-oxo-2,3-dihydro-1H-indol-3-yl]-N,N-dimethyl-1,2,3,4-tetrahydroisoquinoline-3-carboxamide, levorotatory isomer;

(3S)-2-[4-Chloro-1-[(2,4-dimethoxyphenyl)sulphonyl]-3-(2-methoxyphenyl)-5-methyl-2-oxo-2,3-dihydro-1H-indol-3-yl]-N,N-dimethyl-1,2,3,4-tetrahydroisoquinoline-3-carboxamide, levorotatory isomer;

and solvates or hydrates thereof.

7. A process for the preparation of a compound according to claim 1 wherein a compound of formula:

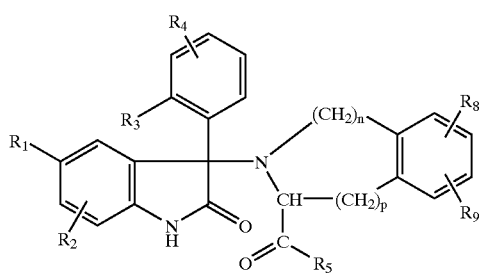
(II)

is reacted, in the presence of a base, with a halide of formula:

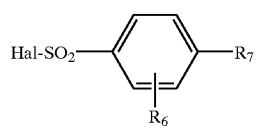
(III)

in which n, p, $R_1$, $R_2$, $R_3$, $R_4$, $R_5$, $R_6$, $R_7$, $R_8$, and $R_9$ are as defined in claim 1 and Hal represents a halogen atom.

8. A compound of formula:

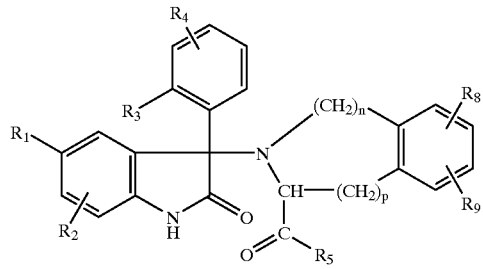
(II)

in which:

n is 0, 1 or 2 and p is 0, 1 or 2; the sum n+p being equal to 1 or 2;

$R_1$ represents a halogen atom; a $(C_1-C_4)$alkyl; a $(C_1-C_4)$alkoxy; a trifluoromethyl radical; or a trifluoromethoxy radical;

$R_2$ represents a hydrogen atom; a halogen atom; a $(C_1-C_4)$alkyl; a $(C_1-C_4)$alkoxy; or a trifluoromethyl radical;

or else $R_2$ is in the 6-position of the indol-2-one ring and $R_1$ and $R_2$ together represent the bivalent trimethylene radical;

$R_3$ represents a halogen atom; a hydroxyl; a $(C_1-C_2)$alkyl; a $(C_1-C_2)$alkoxy; or a trifluoromethoxy radical;

$R_4$ represents a hydrogen atom; a halogen atom; a $(C_1-C_2)$alkyl; or a $(C_1-C_2)$alkoxy;

or else $R_4$ is in the 3-position of the phenyl and $R_3$ and $R_4$ together represent the methylenedioxy radical;

$R_5$ represents an ethylamino group; a dimethylamino group; an azetidin-1-yl radical; or a $(C_1-C_2)$alkoxy;

$R_8$ represents a hydrogen atom; a halogen atom; a $(C_1-C_4)$alkyl; or a $(C_1-C_4)$alkoxy; and $R_9$ represents a a hydrogen atom; a halogen atom; a $(C_1-C_4)$alkyl; or a $(C_1-C_4)$alkoxy;

or a salt thereof with an inorganic or organic acid.

9. A compound according to claim 1 wherein:

the 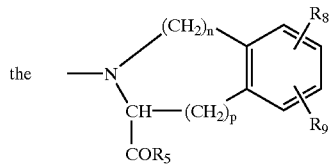

radical represents a radical:

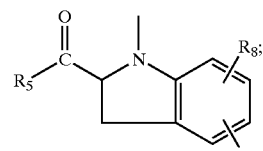
(A)

-continued

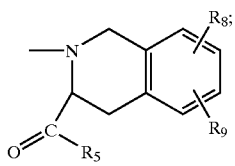
(D)

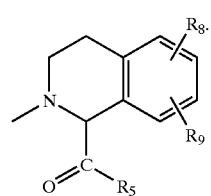
(E)

R₁ represents a chlorine atom or a methyl radical;
R₂ represents a hydrogen atom or is in the 4- or 6-position of the indol-2-one and represents a chlorine atom, a methyl radical or a methoxy radical;
R₃ represents a methoxy radical or a chlorine atom;
R₄ represents a hydrogen atom or is in the 3- or 4-position of the phenyl and represents a methoxy radical;
or else R₄ is in the 3-position of the phenyl and together with R₃ represent a methylenedioxy radical;
R₅ represents a dimethylamino group or a methoxy radical;
R₆ is in the 2-position of the phenyl and represents a methoxy radical;
R₇ represents a methoxy radical; and
R₈ and R₉ represent a hydrogen atom.

10. A compound according to claim 8 in the form of optically pure isomers or in the form of a mixture of diasterioisomers or in the form of a racemic mixture.

11. A pharmaceutical composition comprising a compound according to claim 1 and a pharmaceutically acceptable excipient.

12. A pharmaceutical composition comprising a compound according to claim 3 and a pharmaceutically acceptable excipient.

13. A pharmaceutical composition comprising a compound according to claim 4 and a pharmaceutically acceptable excipient.

14. A pharmaceutical composition comprising a compound according to claim 5 and a pharmaceutically acceptable excipient.

15. A pharmaceutical composition comprising a compound according to claim 6 and a pharmaceutically acceptable excipient.

16. A method for the treatment of a disease in which arginine-vasopressin or its $V_{1b}$ receptors or both its $V_{1b}$ and $V_{1a}$ receptors are involved which comprises administering to a patient in need of such treatment an effective amount of a compound according to claim 1.

17. A method for the treatment of a disease in which arginine-vasopressin or its $V_{1b}$ receptors or both its $V_{1b}$ and $V_{1a}$ receptors are involved which comprises administering to a patient in need of such treatment an effective amount of a compound according to claim 3.

18. A method for the treatment of a disease in which arginine-vasopressin or its $V_{1b}$ receptors or both its $V_{1b}$ and $V_{1a}$ receptors are involved which comprises administering to a patient in need of such treatment an effective amount of a compound according to claim 4.

19. A method for the treatment of a disease in which arginine-vasopressin or its $V_{1b}$ receptors or both its $V_{1b}$ and $V_{1a}$ receptors are involved which comprises administering to a patient in need of such treatment an effective amount of a compound according to claim 5.

20. A method for the treatment of a disease in which arginine-vasopressin or its $V_{1b}$ receptors or both its $V_{1b}$ and $V_{1a}$ receptors are involved which comprises administering to a patient in need of such treatment an effective amount of a compound according to claim 6.

* * * * *